US008603789B2

(12) United States Patent
Harlick

(10) Patent No.: US 8,603,789 B2
(45) Date of Patent: *Dec. 10, 2013

(54) METHOD FOR INTRODUCING CELLULASE ENZYME TO LIGNOCELLULOSIC FEEDSTOCK SLURRY

(75) Inventor: Peter J. E. Harlick, Ontario (CA)

(73) Assignee: Iogen Energy Corporation, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/408,224

(22) Filed: Feb. 29, 2012

(65) Prior Publication Data

US 2012/0237983 A1    Sep. 20, 2012

Related U.S. Application Data

(60) Provisional application No. 61/454,122, filed on Mar. 18, 2011.

(51) Int. Cl.
  *C12P 7/10*  (2006.01)

(52) U.S. Cl.
  USPC ........................................................ 435/165

(58) Field of Classification Search
  USPC .................... 435/165, 105, 207, 209
  See application file for complete search history.

(56) References Cited

U.S. PATENT DOCUMENTS

| 3,308,037 | A | | 3/1967 | Goos et al. | |
|---|---|---|---|---|---|
| 4,409,329 | A | * | 10/1983 | Silver | 435/105 |
| 4,729,664 | A | | 3/1988 | Kamiwano et al. | |
| 5,248,484 | A | | 9/1993 | Scott et al. | |
| 5,498,766 | A | | 3/1996 | Stuart et al. | |
| 5,508,183 | A | | 4/1996 | Scott et al. | |
| 5,801,140 | A | | 9/1998 | Langley et al. | |
| 7,537,826 | B2 | | 5/2009 | Medoff et al. | |
| 2008/0227182 | A1 | * | 9/2008 | Anderson et al. | 435/267 |
| 2009/0312872 | A1 | | 12/2009 | Burris et al. | |
| 2010/0012583 | A1 | | 1/2010 | Stuart | |
| 2010/0221819 | A1 | | 9/2010 | Foody et al. | |
| 2012/0052534 | A1 | * | 3/2012 | Harlick et al. | 435/105 |

FOREIGN PATENT DOCUMENTS

| WO | 88/08855 | 11/1988 |
|---|---|---|
| WO | 2009/045651 | 4/2009 |
| WO | 2010/045168 | 4/2010 |
| WO | 2011/044282 | 4/2011 |

OTHER PUBLICATIONS

Lamsal B. et al. Extrusion as a Thermo Mechanical Pre-Treatment for Lignocellulosic Ethanol. Biomass and Bioenergy vol. 34:1703-10, Aug. 1, 2010.*
Cao, et al., "The Effect of Shear Field on the Hydrolysis of Cellulose", Journal of Macromolecular Science, vol. B43, No. 6 (2004) 1115-21.
Gunjikar, et al., "Shear Deactivation of Cellulase, Exoglucanase, Endoglucanase, and β-Glucosidase in a Mechanically Agitated Reactor", Biotechnol. Prog., vol. 17 (2001) 1166-68.
Gusakov, et al., "Enhancement of Enzymatic Cellulose Hydrolysis Using a Novel Type of Bioreactor with Intensive Stirring Induced by Electromagnetic Field", Applied Biochemistry and Biotechnology, vol. 56 (1996) 141-53.
Mukataka, et al., "Effects of Agitation on Enzymatic Hydrolysis of Cellulose in a Stirred-Tank Reactor", J. Ferment. Technol., vol. 61, No. 6 (1983) 615-21.
Reese, et al., "Shear inactivation of cellulase of *Trichoderma reesei*", Enzyme Microb. Technol., vol. 2 (1980) 239-40.
Samaniuk, et al., "The effect of high intensity mixing on the enzymatic hydrolysis of concentrated cellulose fiber suspensions", Bioresource Technology, vol. 102, No. 6 (2011) 4489-94.
Tolan, et al., "Mill usage and mechanistic studies of xylanase to enhance bleaching", Biotechnology in the Pulp and Paper Industry, vol. 21 (2002) 263-70.

* cited by examiner

*Primary Examiner* — Ralph Gitomer
(74) *Attorney, Agent, or Firm* — Fitzpatrick, Cella, Harper & Scinto

(57) ABSTRACT

The present invention provides a method for producing glucose from a lignocellulosic feedstock. The method comprises moving a pretreated feedstock slurry that has an undissolved solids content of between about 15 and about 30 wt % through a pipe. Cellulase enzyme is added to the pretreated slurry to produce a slurry comprising cellulase enzyme. A high shear in-line mixing device is used to disperse the cellulase enzyme in the pretreated slurry to produce a pretreated slurry comprising dispersed cellulase enzyme. The pretreated slurry comprising dispersed cellulase enzyme is then subjected to hydrolysis so as to produce glucose from cellulose contained therein.

12 Claims, 11 Drawing Sheets

METHOD FOR INTRODUCING CELLULASE ENZYME TO LIGNOCELLULOSIC FEEDSTOCK SLURRY

CROSS-REFERENCE TO RELATED APPLICATIONS

This application claims the priority benefit of provisional application No. 61/454,122, filed Mar. 18, 2011, which is incorporated herein by reference.

TECHNICAL FIELD

The present invention relates to an improved process for converting a lignocellulosic feedstock to glucose. In particular, the present invention relates to an improved process for enzymatically hydrolyzing cellulose to glucose.

BACKGROUND OF THE INVENTION

Much attention and effort has been applied in recent years to the production of fuels and chemicals, primarily ethanol, from cellulosic feedstocks, such as agricultural wastes and forestry wastes, due to their low cost and wide availability. These agricultural and forestry wastes are typically burned and landfilled. Thus, using these cellulosic feedstocks for ethanol production offers an attractive alternative to disposal.

The first chemical processing step for converting cellulosic feedstock to ethanol or other fermentation products usually involves pretreatment of the feedstock. The purpose of the pretreatment is to increase the cellulose surface area, with limited conversion of the cellulose to glucose. Pretreatment of the feedstock can be achieved using an acid pretreatment conducted under conditions that hydrolyse the hemicellulose component of the feedstock, followed by enzymatic hydrolysis of the cellulose remaining in the pretreated cellulosic feedstock with cellulase enzymes. Acid pretreatment typically hydrolyses the hemicellulose component of the feedstock to yield xylose, glucose, galactose, mannose and arabinose and this is thought to improve the accessibility of the cellulose to cellulase enzymes.

In one type of acid pretreatment process, the pressure produced by the steam is brought down rapidly with explosive decompression, which is known as steam explosion. Foody (U.S. Pat. No. 4,461,648) describes the equipment and conditions used in steam explosion pretreatment. Steam explosion with sulfuric acid added to achieve a pH of 0.4 to 2 produces pretreated material that is uniform and requires less cellulase enzyme to hydrolyze cellulose than other pretreatment processes.

Other pretreatment methods have been described in the literature including alkali pretreatment and mechanical pretreatment. Examples of alkaline pretreatment processes include ammonia fiber expansion (AFEX) and dilute ammonia pretreatment. According to the AFEX process, the cellulosic biomass is contacted with ammonia or ammonium hydroxide, which is typically concentrated, in a pressure vessel. Dilute ammonia pretreatment utilizes more dilute solutions of ammonia or ammonium hydroxide than AFEX.

Examples of mechanical pretreatment processes include those disclosed in US 2001/0012583 and in U.S. Pat. No. 5,498,766, which is discussed below. According to these processes, feedstock slurries are fed to a high shear device that comprises multiple concentric rings mounted on a rotor in a chamber. Slurry enters the center of the device and is forced out radially through gaps situated between teeth present in the rings. As the slurry passes through gaps and teeth in the rings, this introduces intense shear and cavitation in the feedstock. As set forth therein, this action increases the surface area of the substrate and disrupts its fiber structure.

The cellulase enzymes utilized to hydrolyze the cellulose to glucose include a mix of enzymes including exo-cellobiohydrolases (CBH), endoglucanases (EG) and beta-glucosidases. The CBH and EG enzymes catalyze the hydrolysis of the cellulose ($\beta$-1,4-D-glucan linkages). The CBH enzymes, CBHI and CBHII, act on the ends of the glucose polymers in cellulose microfibrils and liberate cellobiose, while the EG enzymes act at random locations on the cellulose. Together, the cellulase enzymes hydrolyze cellulose to cellobiose, which, in turn, is hydrolyzed to glucose by beta-glucosidase (beta-G). Enzymatic hydrolysis is typically conducted in one or more dilute mixed batch reactors under controlled pH, temperature and mixing conditions.

The fermentation to produce ethanol from the glucose is typically carried out with a *Saccharomyces* spp. strain. Recovery of the ethanol is achieved by distillation and the ethanol may be further concentrated by molecular sieves.

The addition of water to the incoming feedstock or the pretreated feedstock to form a slurry facilitates the transportation and mechanical handling of the cellulosic feedstock. The slurry consists of cellulosic feedstock or pretreated feedstock pieces or particles in water. In many lignocellulosic conversion processes described in the prior art to produce fermentable sugar, the solids content, measured as undissolved solids (referred to herein as "UDS"), is between 5 and 12 wt %. Such slurries are typically referred to as "medium consistency slurries". The consistency of the aqueous slurry, expressed as the undissolved solids concentration (UDS), may be determined by the UDS procedure described in the examples.

However, for lignocellulosic conversion processes to be more economical, it would be desirable for the slurries to contain a higher undissolved solids content. The processing of slurries containing high solids content has numerous advantages in various stages of the process. For example, during chemical pretreatment, the lower water content in the incoming slurry requires less steam for the heat-up, as well as chemical. During enzymatic hydrolysis, the volumetric efficiency of the process is improved at high solids content. Furthermore, at high solids content, the hydrolysis product will contain a high concentration of fermentable sugars, which improves productivity.

Moreover, reduced volumes of water in the slurry result in reductions in equipment size, which, in turn, reduces capital cost. A further advantage of using high solids consistency slurries is that the amount of water supplied to the plant can be significantly reduced. Water usage adds significant expense to the process, especially in arid climates. Reducing the water requirements for the process would be a major step in making the process more economically viable.

Despite the foregoing advantages associated with utilizing high consistency slurries, the processing of such slurries downstream of pretreatment can pose problems, particularly during the enzymatic hydrolysis of cellulose. One problem that the inventor has identified is that the use of standard equipment to mix cellulase enzyme with pretreated feedstock slurry prior to enzymatic hydrolysis is not effective when the undissolved solids content of the pretreated slurry is high. Such mixing steps conducted prior to enzymatic hydrolysis are required in order to ensure that the cellulase enzyme is adequately dispersed in the pretreated feedstock slurry prior to commencement of enzymatic hydrolysis. A typical equipment configuration is a hydrolysis make-up tank, wherein enzyme and alkali are combined prior to entry of the slurry into the hydrolysis reactor. However, in order for a conventional mix tank to effectively disperse the enzyme in highly viscous slurry, a very large power input is required. This is because the rheological properties of such slurries suggest that the slurry will exhibit semi-solid type behaviour at low stress. Such rheological properties will result in high power requirements, which will significantly increase the operating costs of the hydrolysis stage of the process.

There has been much effort in the development of methods to hydrolyze cellulose to glucose using cellulase enzymes, much of which has focused on dilute systems. U.S. Pat. No. 5,248,484 discloses conducting enzymatic hydrolysis of cellulose in an agitated hydrolyzer that contains an internal stirring device. A side stream is withdrawn from the reactor and sent to an attritor that produces a high shear field for causing attrition or size reduction of the solid particulate. The stream exiting the attritor is then re-circulated back to the agitated hydrolyzer. Such a configuration exposes new substrate surface area to the enzyme so as to increase reaction efficiency. U.S. Pat. No. 5,508,183 discloses a similar equipment configuration for achieving enzymatic hydrolysis of cellulose.

However, the foregoing patents (U.S. Pat. Nos. 5,248,484 and 5,508,183) do not address the problems relating to hydrolyzing cellulose in high consistency systems, specifically the problems associated with introduction of cellulase enzyme to thick slurries. Moreover, the reactor systems disclosed therein would likely not be economically feasible for hydrolyzing cellulose in high consistency slurries. For instance, in order for such stirred reactors to mix a highly viscous slurry effectively during enzymatic hydrolysis, a very large power input would be required.

WO 2009/045651 discloses a fed batch reactor system including multiple size reduction steps and mixing to maintain thorough mixing of high consistency biomass in a vertical, agitated tank. Biomass is introduced into a vertical reactor tank equipped with an overhead agitator system such as a motor and shaft with one or more impellers. A mixable slurry is introduced into the reactor. For slurries without adequate levels of water, liquid is added prior to loading in order to sustain mixing under action of the agitator. The biomass slurry is then reacted under suitable conditions. An additional portion of pretreated biomass is added to the reactor to produce a higher solids biomass slurry as the slurry becomes less viscous as hydrolysis proceeds. Mixability of the slurry is monitored and biomass addition is controlled to maintain thorough mixing. However, the process does not address addition of enzyme to a high consistency slurry, but rather maintaining a high solids content in the reactor so as to achieve high sugar concentrations.

U.S. Pat. No. 4,409,329 discloses contacting an aqueous slurry comprising from 3-20 wt % solid cellulose containing stock with a cellulase enzyme, wherein the contacting occurs in the presence of shear through the reaction zone in a hydrolysis vessel. The vessel contains a concentric shaft which supports a number of perforated rotor blades which alternate with stator blades affixed to the walls of the vessel. However, such a hydrolysis vessel would require a high power input in order to mix high consistency slurries.

U.S. Pat. No. 5,498,766 (supra) discloses a pretreatment stage during which the biomass is shattered, shredded and disintegrated, so as to explode the fibers and rip them apart. It is reported that the resulting fibers exhibit extensive internal decrystallization due to microcavitation and shearing. As described previously, this decrystallization is carried out with a high-frequency, rotor-stator dispersion device having concentric, toothed rings within a chamber. Feedstock enters the center of the device and passes through gaps in the toothed rings due to the centrifugal force exerted by the device. The purpose of the shattering, shearing and disintegration step is to disrupt the lignin bonding to the cellulose and possibly the cellulose bonding to hemicellulose. This renders the cellulose material more available for hydrolysis by cellulase. Cellulase may be added to the slurry before or after exposure to the fiber explosion stage.

Other literature suggests that the activity of cellulases decreases with increasing shear rate or with vigorous mixing. Studies have shown that high shear or prolonged exposure of cellulases to shear during hydrolysis can cause the enzymes to denature (see for example, Cao and Tan, 2004, Journal of Macromolecular Science B43(6):1115-1121).

There is a need for more efficient and cost effective processes for hydrolyzing cellulose to glucose in high consistency slurries. In particular, there is a need in the art to further reduce capital and operating costs associated with such a process so as to make it more commercially feasible.

SUMMARY OF THE INVENTION

The present invention overcomes one or more disadvantages of the prior art by taking into account the difficulties encountered in steps carried out during the processing of lignocellulosic feedstock to obtain glucose.

It is an object of the invention to provide an improved process for enzymatically hydrolyzing cellulose to glucose.

According to one aspect of the present invention, there is provided a method for producing glucose from a lignocellulosic feedstock. The method comprises the steps of: (i) providing a pretreated lignocellulosic feedstock slurry in which at least a portion of the hemicellulose has been hydrolyzed during a pretreatment; (ii) moving the pretreated slurry through a pipe, which slurry has an undissolved solids content of between about 15 and about 30 wt %; (iii) optionally adjusting the pH of the pretreated slurry to a pH that is compatible with cellulase enzyme; (iv) adding cellulase enzyme to the pretreated slurry to produce a slurry comprising cellulase enzyme, while maintaining the undissolved solids content of the pretreated slurry between about 15 and about 30 wt %; (v) dispersing the cellulase enzyme added in step (iv) in the pretreated slurry by using a high shear in-line mixing device so as to impart shear to the pretreated slurry, thereby producing a pretreated slurry in which the cellulase enzyme is dispersed; and thereafter (vi) subjecting the pretreated slurry resulting from step (v) comprising dispersed cellulase enzyme to hydrolysis so as to produce glucose from cellulose contained therein.

According to a further aspect of the invention, there is provided a method, as described above, wherein the high shear in-line mixing device comprises one or more mixing element, wherein the ratio of the cross-sectional area of the one or more mixing element to the cross-sectional area of the pipe in the same lateral plane is between 0.01 and 2.

According to a further aspect of the invention, there is provided a method, as described above, wherein the residence time of the pretreated slurry in the high shear in-line mixing device is between 0.1 s and 60 s.

According to any of the foregoing aspects of the invention, the feedstock slurry may comprise feedstock having at least 20% cellulose and greater than 90% by volume of the feedstock particles have a length between about ⅛ inch and about 6 inches.

According to another embodiment of the invention, the pretreated lignocellulosic feedstock slurry is an acid pretreated lignocellulosic feedstock slurry.

In any of the foregoing aspects of the invention, the cellulase enzyme may be added upstream of the high shear in-line mixing device, adjacent to the high shear in-line mixing device or a combination thereof.

In a further embodiment of the invention, the high shear in-line mixing device is a rotor-stator mixer having mixing elements mounted on a rotatable shaft that extends into the pipe. The high shear in-line mixing device may be a high shear in-line mixer, as defined hereinafter.

In one embodiment of the invention, the shear rate imparted to the pretreated feedstock is between 10 and 10,000 $s^{-1}$, or between 100 and 1,000 $s^{-1}$.

According to one embodiment of the invention, the step of subjecting the pretreated slurry to hydrolysis may comprise feeding the pretreated slurry in which the cellulase enzyme is dispersed to at least one unmixed hydrolysis reactor, mixed hydrolysis reactor or a combination thereof.

According to a further aspect of the invention, there is provided a system for producing glucose from a lignocellulosic feedstock. The system comprises: (i) a pretreatment reactor for receiving the lignocellulosic feedstock slurry and hydrolyzing hemicellulose present in the feedstock therein, thereby producing a pretreated lignocellulosic feedstock; (ii) an enzyme addition device downstream of the pretreatment reactor for adding cellulase enzyme to the pretreated lignocellulosic feedstock; (iii) a pipe for receiving the pretreated feedstock and a high shear in-line mixer for receiving and imparting shear to the pretreated slurry, thereby producing a pretreated slurry in which the cellulase enzyme is dispersed; (iv) one or more unmixed hydrolysis reactors for receiving and partially hydrolyzing the pretreated slurry in which the cellulase enzyme is dispersed so as to produce a mixture of partially hydrolyzed cellulose; and (v) one or more downstream mixed hydrolysis reactors for receiving the partially hydrolyzed cellulose and continuing the hydrolysis of the mixture to produce the glucose.

The system may further comprise a dewatering device upstream or downstream of the pretreatment reactor for receiving and dewatering the lignocellulosic feedstock slurry.

According to a further aspect of the invention, there is provided a method for producing glucose from a lignocellulosic feedstock, the method comprising the steps of: (i) providing a pretreated lignocellulosic feedstock slurry; (ii) moving the pretreated feedstock slurry through a pipe, which slurry has an undissolved solids content of between about 15 and about 30 wt %; (iii) adding cellulase enzyme to the pretreated slurry to produce a slurry comprising cellulase enzyme; (iv) dispersing the cellulase enzyme added in step (iii) in the pretreated slurry by using a high shear in-line mixing device, thereby producing a pretreated slurry comprising dispersed cellulase enzyme; and thereafter (v) subjecting the pretreated slurry comprising dispersed cellulase enzyme to hydrolysis so as to produce glucose from cellulose contained therein. In one embodiment of this aspect of the invention, the mixing device is a high shear in-line mixer.

The present invention can provide numerous benefits over conventional processes involving the conversion of cellulose to glucose. Disclosed herein is a method to disperse cellulase enzymes in high consistency slurries with reduced power requirements by the use of an in-line high shear mixer. Reducing the operating costs associated with dispersing enzyme to high consistency slurries prior to enzymatic hydrolysis could be a significant step forward with respect to commercialization of processes for producing glucose from lignocellulosic feedstock.

BRIEF DESCRIPTION OF THE DRAWINGS

FIG. 1A illustrates the dissection of the sample into three sections and FIG. 1B illustrates the dissection of the sample into 8 sections. Each section was subsequently assayed for potassium iodide concentration (excluding the middle section of FIG. 1B).

DETAILED DESCRIPTION OF THE INVENTION

Figure 1A:
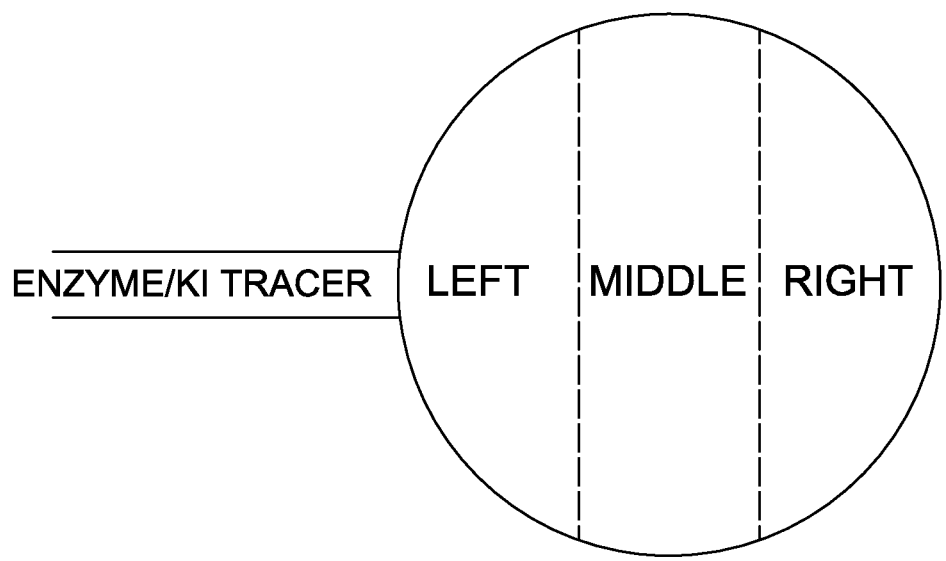
FIGS. 1A and 1B depict cross-sectional slices of a high consistency acid pretreated lignocellulosic feedstock (undissolved solids content of 21 wt %) sampled downstream of an in-line high shear mixer after addition of potassium iodide tracer upstream of the mixer.

The following description is of a preferred embodiment by way of example only and without limitation to the combination of features necessary for carrying the invention into effect. The headings provided are not meant to be limiting of the various embodiments of the invention. Terms such as "comprises", "comprising", "comprise", "includes", "including" and "include" are not meant to be limiting. In addition, the use of the singular includes the plural, and "or" means "and/or" unless otherwise stated. Unless otherwise defined herein, all technical and scientific terms used herein have the same meaning as commonly understood by one of ordinary skill in the art.

Description of Feedstock Types

The feedstock for the process is a lignocellulosic material. By the term "lignocellulosic feedstock", it is meant any type of plant biomass such as, but not limited to, non-woody plant biomass, cultivated crops such as, but not limited to grasses, for example, but not limited to, C4 grasses, such as switch grass, cord grass, rye grass, miscanthus, reed canary grass, or a combination thereof, sugar processing residues, for example, but not limited to, baggase bagasse, such as sugar cane bagasse, beet pulp, or a combination thereof, agricultural residues, for example, but not limited to, soybean stover, corn stover, rice straw, sugar cane straw, rice hulls, barley straw, corn cobs, wheat straw, canola straw, oat straw, oat hulls, corn fiber, or a combination thereof, forestry biomass for example, but not limited to, recycled wood pulp fiber, sawdust, hardwood, for example aspen wood, softwood, or a combination thereof. Furthermore, the lignocellulosic feedstock may comprise lignocellulosic waste material or forestry waste materials such as, but not limited to, newsprint, cardboard and the like. Lignocellulosic feedstock may comprise one species of fiber or, alternatively, lignocellulosic feedstock may comprise a mixture of fibers that originate from different lignocellulosic feedstocks. In addition, the lignocellulosic feedstock may comprise fresh lignocellulosic feedstock, partially dried lignocellulosic feedstock, fully dried lignocellulosic feedstock, or a combination thereof. Moreover, new lignocellulosic feedstock varieties may be produced from any of those listed above by plant breeding or by genetic engineering.

Lignocellulosic feedstocks comprise cellulose in an amount greater than about 20%, more preferably greater than about 30%, more preferably greater than about 40% (w/w). For example, the lignocellulosic material may comprise from about 20% to about 50% (w/w) cellulose, or any amount therebetween. Furthermore, the lignocellulosic feedstock comprises lignin in an amount greater than about 10%, more typically in an amount greater than about 15% (w/w). The lignocellulosic feedstock may also comprise small amounts of sucrose, fructose and starch.

Feedstock Size Reduction

The lignocellulosic feedstock is generally first subjected to size reduction by methods including, but not limited to, milling, grinding, agitation, shredding, compression/expansion, or other types of mechanical action. According to the invention, the lignocellulosic feedstock from the size reduction process produces a size-reduced feedstock comprising particles of a defined length. At least 90% by volume of the size reduced feedstock have a length less than between about ⅛ and about 6 inches. As would be appreciated by those of ordinary skill in the art, lignocellulosic feedstock that has been subjected to size reduction comprises feedstock particles having a range of sizes and shapes.

Size reduction by mechanical action can be performed by any type of equipment adapted for the purpose, for example, but not limited to, hammer mills, tub-grinders, roll presses, refiners, shredders and hydrapulpers. The preferable equipment for the particle size reduction is a hammer mill, tub grinder, an "SSI Shredder" commercially available from SSI Shredding Systems, Wilsonville, Oreg. or a "Grizzly Shredder" available from Granutech-Saturn Systems International, Grand Prairie, Tex.

It should be appreciated that the lignocellulosic feedstock need not be subjected to size reduction if the particle size of the feedstock is already between ½ to 6 inches.

If size reduction is required, it can be performed while the lignocellulosic feedstock is dry or moist, i.e., having a moisture content of 0% to 20%, or while water is added to the lignocellulosic feedstock. Dry shredding can be carried out, for example, with an SSI or Grizzly shredder, hammer mill or tub grinder, while wet shredding may be performed with pulpers. When dry shredding is employed, the particle size may be between ½ to 6 inches. When hammer milling, the particle size may be less than 4 inches to less than ½ inch depending on the size of the screens used in the hammer mill.

The size of the lignocellulosic feedstock particles can have an impact on both processing of the feedstock and in the chemical reactions involved during pretreatment. As discussed hereinafter, when the lignocellulosic feedstock particles are mixed with liquid the resultant mass is often characterized as a feedstock slurry. The feedstock slurry may be processed in equipment typically used to process liquid streams. A person of ordinary skill in the art could select a concentration of feedstock particles and particle characteristics that allows for ease of processing and that achieves a desired reactivity of the feedstock in acid pretreatment.

For the purposes of this specification, the size of the feedstock particles is determined by image analysis using techniques known to those of ordinary skill in the art. An example of a suitable image analysis technique is disclosed in Igathinathane (Sieveless particle size distribution analysis of particulate materials through computer vision, Computers and Electronics in Agriculture, 2009, 66:147-158), which reports particle size analyses of several different hammer milled feedstocks. The measurement may be a volume or a weight average length.

Washing of the feedstock may be carried out to remove sand, grit and other foreign particles as they can cause damage to the downstream equipment.

Feedstock Slurry Preparation

Slurrying of the feedstock allows it to be pumped readily and may be carried out in any suitable batch or continuous mixing vessel, including a standpipe or pulper. Slurrying may be distinct from the water and chemical addition or may occur simultaneously therewith.

Slurrying of the incoming feedstock can occur at any suitable consistency selected by those of ordinary skill in the art. In practice, the consistency of the feedstock slurry utilized will depend on the specific mixing means employed and the specific pumps used. The consistency of the aqueous slurry of the lignocellulosic feedstock is expressed as the undissolved solids concentration (UDS), which is determined by the UDS procedure described in the examples.

In one embodiment of the invention, the consistency of the feedstock slurry is between about 2% and about 40% undissolved solids (w/w) or more typically between about 4% and about 20% undissolved solids (w/w).

Reference may be made to the "Handbook of Industrial Mixing" (Ed. Paul, Atiemo-Obeng, Kresta, 2004, Wiley-Interscience, Hoboken, N.J., incorporated herein by reference), which provides an introduction to the equipment and critical parameters of mixing performance and design. (See, for example, Chapters 10, 17 and 18 that particularly focus on solid-liquid mixing).

The lignocellulosic feedstock contains leachable minerals, such as potassium, sodium, calcium and, in some instances, magnesium. The feedstock is optionally leached prior to dilute acid pretreatment to remove these substances from the feedstock. By leaching the lignocellulosic feedstock, the level of compounds that increase acid demand during dilute acid pretreatment is reduced.

Dewatering Prior to Acid Pretreatment

The lignocellulosic feedstock may subsequently be dewatered by any suitable technique known to those of ordinary skill in the art. For instance, dewatering may be effected by utilizing devices that remove water under pressure from the aqueous feedstock slurry. Dewatering devices suitable for use in the invention includes pressurized screw presses, such as those described in WO 2010/022511 (incorporated herein by reference) and pressurized filters. The dewatering process optionally includes a pre-draining zone in order to drain out water from the feedstock slurry at atmospheric pressure or higher. This dewatered feedstock slurry is then sent to one or more devices for dewatering the slurry under pressure. Water expressed from the cellulosic feedstock by the dewatering step may be reused in the process.

The feedstock slurry may be fed to the pressurized dewatering device via one or more high pressure pumps, such as those available from Sulzer Corp. or Andritz AG, or by other suitable feeding devices. The pump or other feeding device increases the pressure of the feedstock slurry to e.g., about 70 psia to about 900 psia. The pressure may be measured with a pressure sensor located at the inlet on the dewatering device.

Pretreatment of the Lignocellulosic Feedstock

The pretreatment disrupts the fiber structure of the lignocellulosic feedstock and increases the surface area of the feedstock to make it accessible to cellulase enzymes. Preferably, the pretreatment is performed so that a high degree of hydrolysis of the hemicellulose and only a small amount of conversion of cellulose to glucose occurs. The cellulose is hydrolyzed to glucose in a subsequent step that uses cellulase enzymes.

Acid pretreatment is preferably carried out at a maximum temperature of about 160° C. to about 280° C., or any range therebetween. For example, the temperature may be about 160, 170, 180, 190, 200, 210, 220, 230, 240, 250, 260, 270 or 280° C. It should be understood that, in practice, there will be a time delay in the pretreatment process before the feedstock reaches this temperature range. Thus, the above temperatures correspond to those values reached after sufficient application of heat to reach a temperature within this range.

The ideal retention time in the pretreatment reactor will vary depending on the temperature, acid concentration, feedstock used, and the degree of treatment desired. For example, the slurry could be retained in the pretreatment reactor for about 0.5 to about 10 minutes, or any time therebetween. That is, the retention time may be about 0.5, 1, 1.5, 2, 2.5, 3, 3.5, 4, 4.5, 5, 5.5, 6, 6.5, 7, 7.5, 8, 8.5, 9, 9.5 or 10 minutes. It should be appreciated that the particles are not all retained for the same time period. The ideal retention time is reactor volume (L) divided by the flow rate (L/min).

The pretreatment is typically carried out under pressure. For example, the maximum pressure during pretreatment may be between about 50 and about 700 psig or between about 75 and about 600 psig, or any pressure range therebetween.

If acid is employed for pretreatment it may be sulfuric acid, sulfurous acid, hydrochloric acid or phosphoric acid. Preferably, the acid is sulfuric acid. The amount of acid added to the lignocellulosic feedstock may vary, but should be sufficient to achieve a final concentration of acid in the slurry of about 0.02 wt % to about 2 wt %, or any amount therebetween. The resulting pH of the feedstock is about pH 0.4 to about pH 3.5, or any pH range therebetween. For example, the pH of the slurry may be between about 0.4, 1.0, 1.5, 2.0, 2.5, 3.0 or 3.5.

The extent of xylan hydrolysis may be between about 80-100 wt %, or any range therebetween. A suitable pH and temperature can be selected within this pH range to hydrolyze at least about 80 wt % of the xylan, while maintaining the degree of cellulose hydrolysis at 3-15 wt %.

The feedstock may be heated with steam during or prior to pretreatment. Without being limiting, one method to carry this out is to use low pressure steam to partially heat the feedstock, which is then pumped to a heating train of several stages. Other methods may be employed to heat the feedstock, such as commercially available steam mixing devices designed for introducing steam and optionally acid through spray nozzles.

Without being limiting, pretreating of the feedstock may involve continuous pretreatment, meaning that the lignocellulosic feedstock is pumped through a reactor continuously. Continuous acid pretreatment is familiar to those skilled in the art.

The pretreated feedstock to which enzyme is added is present as a slurry, referred to herein as a pretreated feedstock slurry. Sufficient water may be added to the feedstock before or after pretreatment to produce a slurry that is pumpable.

Sugars produced by the hydrolysis of hemicellulose during acid pretreatment are generally present in the slurry and include xylose, glucose, arabinose, mannose, galactose or a combination thereof. Organic acids may be present in the slurry as well and may include acetic acid, galacturonic acid, formic acid, lactic acid, glucuronic acid or a combination thereof. Many lignocellulosic feedstocks contain hemicellulose with acetyl groups attached to xylan. Pretreatment processes liberate acetic acid from the acetyl groups.

According to one exemplary embodiment of the invention, the soluble components of the pretreated feedstock slurry are separated from the solids. This separation may be carried out by washing the pretreated feedstock composition with an aqueous solution to produce a wash stream, and a solids stream comprising the unhydrolyzed, pretreated feedstock. Alternatively, the soluble component is separated from the solids by subjecting the pretreated feedstock slurry to a solids-liquid separation, using known methods such as centrifugation, microfiltration, plate and frame filtration, cross-flow filtration, pressure filtration, vacuum filtration and the like. Optionally, a washing step may be incorporated into the solids-liquids separation. The separated solids, which contain cellulose, may then be sent to enzymatic hydrolysis with cellulase enzymes in order to convert the cellulose to glucose. The enzymatic hydrolysis of cellulose using cellulase enzymes is described in more detail hereinafter.

The aqueous stream, which includes the sugars released during pretreatment, the pretreatment chemical and other soluble components, may then be fermented using a microorganism capable of fermenting the sugars derived from the hemicellulose component of the feedstock.

Subsequent to pretreatment, the pretreated feedstock slurry is typically cooled to decrease its temperature to a range at which the cellulase enzymes are active. It should be appreciated that cooling of the feedstock can occur in a number of stages utilizing flashing, heat exchange or other suitable means.

After pretreatment, the pretreated feedstock slurry is moved through a pipe. Transport of the feedstock slurry through the pipe may be accomplished by a pump that can handle slurries having an undissolved solids concentration of between 15 and 30 wt %. An example of a suitable pump is a progressive cavity pump, such as a Liberty Process progressive cavity pump, commercially available from Liberty Process Equipment.

Enzyme Addition

Subsequent to acid pretreatment, cellulase enzymes are added to the pretreated slurry to produce a slurry comprising cellulase enzyme.

Any type of cellulase enzymes suitable for hydrolyzing cellulose that are effective at the pH and other conditions utilized herein can be used in the practice of the invention, regardless of their source. Cellulases suitable for use in the practice of the invention include those obtained from fungi of the genera *Aspergillus, Humicola, Chrysosporium, Melanocarpus, Myceliopthora, Sporotrichum* and *Trichoderma*, and from the bacteria of the genera *Bacillus* and *Thermobifida*. According to one embodiment, the cellulase is obtained from a fungal source. Cellulase produced by the filamentous fungi *Trichoderma longibrachiatum* comprises at least two cellobiohydrolase enzymes termed CBHI and CBHII and at least four EG enzymes. See Lynd et al., 2002, Microbiology and Molecular Biology Reviews, 66(3):506-577 for a review of cellulase enzyme systems and Coutinho and Henrissat, 1999, "Carbohydrate-active enzymes: an integrated database approach." In Recent Advances in Carbohydrate Bioengineering, Gilbert, Davies, Henrissat and Svensson eds., The Royal Society of Chemistry, Cambridge, pp. 3-12, each of which are incorporated herein by reference.

As would be appreciated by those of skill in the art, in addition to CBH, EG and beta-glucosidase, there are several accessory enzymes present in cellulase preparations that aid in the enzymatic digestion of cellulose (see co-owned WO 2009/026722 (Scott), which is incorporated herein by reference, and Harris et al., 2010, Biochemistry, 49:3305-3316). These include EGIV, also known as Cel61, swollenin, expansin, lucinen and cellulose-induced protein (Cip).

The conversion of cellobiose to glucose is carried out by the enzyme β-glucosidase. By the term "β-glucosidase", it is meant any enzyme that hydrolyzes the glucose dimer, cellobiose, to glucose. The activity of the β-glucosidase enzyme is defined by its activity by the Enzyme Commission as EC#3.2.1.21. The β-glucosidase enzyme may come from various sources; however, in all cases, the β-glucosidase enzyme can hydrolyze cellobiose to glucose. The β-glucosidase enzyme may be a Family 1 or Family 3 glycoside hydrolase, although other family members may be used in the practice of this invention. The preferred β-glucosidase enzyme for use in this invention is the Bgl1 protein from *Trichoderma reesei*. It is also contemplated that the β-glucosidase enzyme may be modified to include a cellulose binding domain, thereby allowing this enzyme to bind to cellulose.

The pretreated lignocellulosic feedstock slurry to which the cellulase enzyme is added is a high consistency slurry, meaning that it has between about 15 wt % and about 30 wt % undissolved solids (UDS) or any range therebetween. In another embodiment of the invention, the pretreated lignocellulosic feedstock slurry has between about 18 and about 30 wt % or between about 18 wt % and about 28 wt % UDS, or any range therebetween. The range may contain numerical limits of 15, 16, 17, 18, 19, 20, 21, 22, 23, 24, 25, 26, 27, 28, 29 or 30% (w/w). The undissolved solids content is based on dry weight of the solids and is measured according to the procedure set forth in the Examples. The undissolved solids concentration is measured after pretreatment and after the pretreated slurry is cooled.

Cellulase enzyme addition may be carried out by injection at one or optionally two or more locations, typically within the pipe. The enzyme addition site may be in the center of the pipe, the side-wall of the pipe or any other suitable location within the pipe. The enzyme addition may also be carried out by introducing enzyme through two opposing addition points, extending from opposite sides of the pipe, as shown, for example, in FIG. 7. Multiple injection points may also be located at spaced-apart addition points along the length of the pipe.

Enzyme may be added to the slurry by known injection devices. This includes, but is not limited to chemical injection quills, which are commercially available. Alternatively, enzyme may be injected into the slurry through appropriately sized tubing or via a pipe. Typically, the enzyme addition will be carried out so that the introduction point is perpendicular to the flow of slurry.

In one non-limiting example of the invention, enzyme addition is carried out by adding the enzyme to a reservoir, such as a tank, to form an enzyme solution, which is then introduced to the slurry.

Cellulase enzyme addition can be upstream of the high shear in-line mixer, to the in-line mixer, or at both locations. In some embodiments of the invention, the location of enzyme addition is adjacent to the in-line mixer, although upstream enzyme addition is most suitable when carrying out the process of the invention.

The enzymatic hydrolysis with cellulase enzymes is generally conducted at a pH between about 4.0 and 6.0 as this is within the optimal pH range of most cellulases. Thus, the pH of the pretreated feedstock slurry is adjusted upwardly with alkali prior to enzymatic hydrolysis to achieve this pH when the pretreated feedstock is acidic. However, cellulases with pH optima at more acidic and more alkaline pH values could be utilized.

Alkali addition is typically upstream of the cellulase enzyme addition point to ensure that the enzyme is exposed to a pH at which the enzyme is compatible.

High Shear in-Line Mixing

After cellulase enzyme addition, as described above, the enzyme will not be adequately mixed within the high consistency slurry. Mixing of the enzyme with the high shear in-line mixing device is carried out so as to cause uniform dispersion of the enzyme throughout the slurry so that the subsequent enzymatic hydrolysis of cellulose to glucose can proceed efficiently and provide adequate glucose yield. A suitable shear rate is selected so as to ensure enzyme dispersion throughout the pretreated slurry, as discussed below.

Feedstock slurry undergoes shear when one area of the slurry travels with a different velocity relative to an adjacent area. A high shear in-line mixing device may use a high speed rotor device or other configurations, described below, usually powered by an electric motor, to "work" the slurry, creating flow and shear. In devices employing a rotor, the velocity, or tip speed of the fluid at the outside diameter of the rotor will be higher than the velocity at the centre of the rotor, and it is this action that creates shear.

As used herein, the term "high shear in-line mixing device" or "mixing device" refers to any suitable mixing device that imparts shear to the pretreated feedstock slurry at the shear rates set forth herein. The high shear in-line mixing device comprises mixing elements that extend into the line and direction of slurry flow at any location in the slurry as it moves from pretreatment to enzymatic hydrolysis. The mixing elements may extend into the slurry perpendicular to its flow, or they may extend into the slurry at an angle off-set from perpendicular.

As used herein, the term "high shear in-line mixer" or "mixer" refers to a mixing device that does not cause a significant increase in pipe-line pressure relative to the inlet pressure of the slurry fed to the mixer, as would occur in a pump. High shear in-line mixers that are particularly suitable for use in the invention include those that comprise discrete mixing elements that are mounted on a shaft. The mixing elements are capable of moving through the slurry and imparting shear to the slurry as the slurry moves through the mixer. In an in-line high shear rotor-stator mixer, the rotor is contained in a housing with an inlet at an outlet, where the rotor is driven through a pipe line seal. Such devices further comprise a motor and a gear box for driving the rotor. It is contemplated that static mixers could be employed in the practice of the invention as well.

As used herein, the term "mixing element" refers to a structure or structures mounted on a rotatable shaft or a stationary element, which impart shear to the pretreated lignocellulosic feedstock slurry as it flows through the mixing device or mixer. Mixing elements that may be used in accordance with the invention include, but are not limited to, arms, anchors, helixes, hydrofoils, and claws.

The high shear in-line mixing device or high shear in-line mixer optimally does not significantly impede slurry flow as the slurry moves therethrough. If a large negative pressure difference occurs across the mixing device or mixer, this will increase upstream or downstream pumping requirements, which, in turn, increases the power input and pump sizing. The cross-sectional area available for slurry flow in the vicinity of the mixing elements is large enough to ensure that are no restrictions or impediments to slurry flow through the mixing device or mixer. The configuration of the high shear in-line mixing device or mixer is such that the ratio of the cross-sectional area of the mixing element to the cross-sectional area of the pipe in the same lateral plane is small enough so as to ensure adequate slurry flow therethrough. As used herein, the "surface area of the mixing element" is the maximum projected surface area of the mixing element(s) perpendicular to the slurry flow. In some embodiments of the invention, the high shear in-line mixing device or mixer has a ratio of the cross-sectional area of the mixing element to the cross-sectional area of the pipe of between about 0.01 and about 2, or between about 0.1 and about 1.5 or between about 0.2 and about 1.0.

A further method for determining whether or not an in-line mixing device or mixer allows for sufficient slurry flow is to determine the residence time of the slurry in the high shear in-line mixer. The residence time of the slurry in the high shear in-line mixing device or mixer can be determined by either liquid and/or solid phase tracers. The residence time in the high shear in-line mixing device or mixer is determined by the following equation:

$$\text{Ideal mean residence time} = \frac{V}{Q}$$

Where V is the volume swept by the high shear in-line mixing device in $m^3$ or mixer and Q in $m^3/h$ is the flow rate through the high shear in-line mixing device or mixer. In embodiments of the invention, the residence time of the slurry in the high shear in-line mixing device or mixer is between 0.1 and 60 s, or any value therebetween. For example, the residence time of the slurry may be 0.1, 10, 20, 30, 40, 50 or 60 s.

A non-limiting example of a suitable high shear in-line mixing device is a Sulzer® SX-HP-8-8 high shear in-line mixer. Such mixers comprise arms mounted on a rotatable shaft that is installed perpendicular to the direction of flow within the pipe.

Devices are known in which high shear mixing takes place via single or multiple passes through a rotor-stator array to produce particles of a narrow size distribution. To achieve this, the machine is equipped with stators having holes or slots through which the slurry is forced by the rotors. Such devices are disclosed in U.S. Pat. No. 5,498,766 (supra). The mixer disclosed therein is not typically effective at dispersing cellulase enzymes in the acid pretreated feedstock slurries described herein as they are prone to plugging. However, it is contemplated that such devices could be configured so as to avoid such plugging and allow a degree of mixing and shear.

The shear rate imparted to the pretreated lignocellulosic feedstock by the high shear in-line mixing device or mixer may be between 10 and 10,000 $s^{-1}$ or between 100 and 5,000 $s^{-1}$ or between 100 and 2000 $s^{-1}$. The shear rate ($\dot{\gamma}$, measured in $s^{-1}$) is calculated using the following equation:

$$\dot{\gamma} = \frac{N \cdot D}{h}$$

where N is the speed (in revolutions/s), D is the maximum diameter of the mixing element (in meters or inches), d is the diameter (in meters or inches) of the housing of the mixing device or mixer and h is (d−D)/2.

Figure 11:
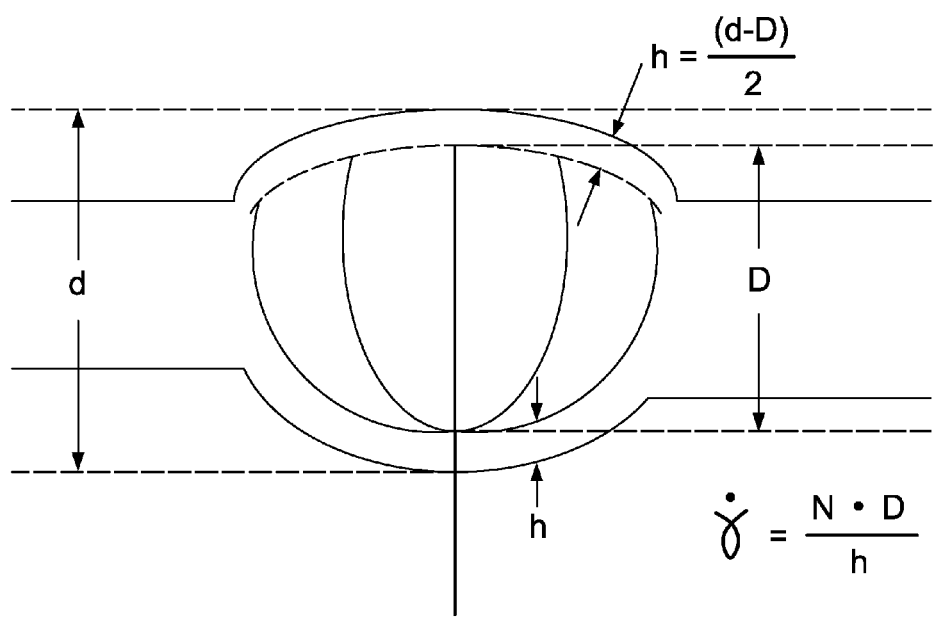
FIG. 11 is a diagram depicting a high shear in-line mixer to illustrate the calculation of shear rate.

For example, consider a mixer installed into a pipe that contains a shaft mounted within a housing, which shaft is perpendicular to the flow of the slurry and comprises arms mounted thereon for mixing and imparting shear to the pretreated slurry. Such a device is depicted in FIG. 11. If the speed (N) of the mixing device is 100 rev/s, the diameter (D) of the housing is 10 inches and the maximum mixing element diameter (D) is 9.75 inches, then the shear rate is 8000 $s^{-1}$= (100*10/0.125). The maximum mixing element diameter is the length of the longest mixing element, i.e., measured from its base to its tip, as shown in FIG. 11.

Enzymatic Hydrolysis

Subsequent to high shear in-line mixing of the cellulase enzyme, the pretreated lignocellulosic feedstock slurry comprising dispersed cellulase enzyme may be fed to one or more unmixed hydrolysis reactor, mixed hydrolysis reactor or a combination thereof. The reactors may be operated in batch, continuous, fed-batch modes, or a combination thereof.

Mixing in the mixed hydrolysis reactor(s) may be achieved by any conventional means, including mechanical mixers such as top-mounted, side-mounted, or bottom-mounted impellers, agitators or eductors; rapid movement of liquid slurry streams pumped into or through the vessel; and/or introducing or generating gases or vapours in the vessel.

A particularly suitable mixed hydrolysis reactor is a continuous stirred-tank reactor (CSTR reactor).

When the hydrolysis is carried out in a mixed hydrolysis system that includes multiple mixed hydrolysis reactors, the number of mixed hydrolysis reactors in the system depends on the cost of the reactors, the volume of the aqueous slurry, and other factors. For a commercial-scale plant, the typical number of hydrolysis reactors may be for example, 3 to 12. Preferably, the mixed enzymatic hydrolysis is a continuous process, with continuous feeding of pretreated cellulosic feedstock and withdrawal of the glucose. However, it should be understood that batch and fed-batch processes, or a combination of these, are also included within the scope of the present invention.

Other design parameters of the mixed hydrolysis reactor(s) may be adjusted as required. For example, the volume of a mixed hydrolysis reactor in a cellulase hydrolysis system can range from about 100,000 L to about 20,000,000 L, or any volume therebetween, for example, between 200,000 and 5,000,000 L, or any amount therebetween. The total residence time of the slurry in a hydrolysis system may be between about 12 hours to about 300 hours, or any amount therebetween.

By the term "unmixed hydrolysis reactor", it is meant a reactor suitable for conducting an enzymatic hydrolysis with cellulase enzymes therein that does not carry out any active mixing of its contents as is typically employed in mixed hydrolysis reactors. Although the unmixed reactor of the present invention may operate with a certain amount of localized mixing due to the introduction and withdrawal of liquid and solids from the system, such localized mixing does not result in any significant dispersal or blending of the reactor contents, as would occur in mixed reactors. For example, a small amount of localized mixing may occur at the bottom of an unmixed downflow reactor due to the action of a rotary bottom scraper or other devices employed for removing the reactor contents. Similarly, if the unmixed reactor is an upflow reactor, a small amount of localized mixing may occur at the top of the unmixed reactor due to the withdrawal of the slurry. The power required for the discharge of the slurry is less than 5%, 3% or 1% of the power required to fully mix the slurry using a mixed reactor of conventional hydrofoil impeller design. A suitable height-to-diameter ratio of an unmixed batch or continuous hydrolysis reactor is between about 0.2:1.0 to about 5.0:1.0, or any ratio therebetween.

The number of unmixed hydrolysis reactors in the system depends on the cost of the reactors, the volume of the aqueous slurry, and other factors. For a commercial-scale plant, the typical number of unmixed hydrolysis reactors may be, for example, 1 to 10.

The unmixed reactors can be in a consecutive or parallel configuration. Those of ordinary skill in the art could readily select a suitable option by weighing the advantages and disadvantages of each design scheme.

Other design parameters of the unmixed hydrolysis reactor(s) may be adjusted as required. For example, the volume of a unmixed hydrolysis reactor in a cellulase hydrolysis system can range from about 100,000 L to about 30,000,000 L, or any volume therebetween, for example, between 200,000 and 5,000,000 L, or any amount therebetween. The total residence time of the slurry in a hydrolysis system may be between about 12 hours to about 300 hours, or any amount therebetween.

According to one particularly advantageous embodiment of the invention, the pretreated lignocellulosic feedstock comprising dispersed cellulase enzyme is fed to one or more unmixed hydrolysis reactor, as described above, to produce a mixture of partially hydrolyzed cellulose. The mixture of partially hydrolyzed cellulose may subsequently be fed to one or more hydrolysis reactors that hydrolyze the feedstock with mixing, as also described previously. In the one or more unmixed reactor, the enzymatic hydrolysis of the cellulose reduces the viscosity of the pretreated cellulosic feedstock. By reducing the viscosity of the pretreated feedstock using enzymatic hydrolysis, the power requirements associated with mixing are reduced during hydrolysis of the mixture of partially hydrolyzed cellulose in the subsequent mixed hydrolysis reactor(s). Such a hydrolysis reactor configuration is described in co-owned and co-pending, U.S. Application Ser. No. 61/378,523 (Harlick), the contents of which are incorporated herein by reference.

After the unmixed hydrolysis is complete, the product is glucose and any unreacted cellulose. Insoluble solids present in the resulting stream, including lignin, may be removed using conventional solid-liquid separation techniques prior to any further processing. However, it may be desirable in some circumstances to carry forward both the solids and liquids in the sugar stream for further processing.

Subsequent to the unmixed hydrolysis, the mixture of partially hydrolyzed cellulose from the unmixed hydrolysis may be introduced to one or more hydrolysis reactors that effect mixing of the slurry. Typically, the slurry is introduced into a mixed hydrolysis reactor by a pump.

Optionally, additional cellulase enzyme can be added during the mixed hydrolysis.

After the mixed hydrolysis is complete, the product is glucose and any unreacted cellulose. Insoluble solids present in the resulting stream, including lignin, may be removed using conventional solid-liquid separation techniques prior to any further processing. However, it may be desirable in some circumstances to carry forward both the solids and liquids in the sugar stream for further processing.

An appropriate cellulase dosage for the mixed or unmixed hydrolysis can be about 1.0 to about 40.0 Filter Paper Units (FPU or IU) per gram of cellulose, or any amount therebetween. The FPU is a standard measurement familiar to those skilled in the art and is defined and measured according to Ghose (Pure and Appl. Chem., 1987, 59:257-268; which is incorporated herein by reference). A preferred cellulase dosage is about 10 to 20 FPU per gram cellulose.

As discussed previously, the enzymatic hydrolysis in the unmixed or mixed hydrolysis is generally conducted at a pH between about 4.0 and 6.0 as this is within the optimal pH range of most cellulases. If the slurry is more acidic, the pH should be increased. The alkali can be added to the pretreated feedstock after it is cooled, before cooling, or at points both before and after cooling. The alkali is typically added upstream of the high shear in-line mixing device or mixer, as described previously. However, further pH adjustments can be carried out pump downstream of enzyme addition, such as directly to a hydrolysis vessel.

Examples of alkali include ammonia, ammonium hydroxide, potassium hydroxide, sodium hydroxide, potassium carbonate, potassium bicarbonate, sodium carbonate, sodium bicarbonate, calcium hydroxide, calcium carbonate or a mixture thereof.

The temperature of the slurry in the mixed or unmixed hydrolysis is adjusted so that it is within the optimum range for the activity of the cellulase enzymes. Generally, a temperature of about 45° C. to about 70° C., or about 45° C. to about 65° C., or any temperature therebetween, is suitable for most cellulase enzymes. However, the temperature of the slurry may be higher for thermophilic cellulase enzymes.

In order to maintain the desired hydrolysis temperature, the contents of the mixed or unmixed hydrolysis reactor(s) are optionally heated or cooled. Heating or cooling may be carried out with heating or cooling jackets or by heat exchange with re-circulated slurry. The heating or cooling fluid used in the heat exchanger or in the jacket may include steam, hot water, cold water, glycol or brine. It should be understood that the temperature of the mixed or unmixed reactor contents during hydrolysis could be maintained within a desired range without any heating or cooling of the reactor contents.

It is preferred that enzymatic hydrolysis and fermentation are conducted in separate vessels so that each biological reaction can occur at its respective optimal temperature. However, the hydrolysis may be conducted simultaneously with fermentation in a simultaneous saccharification and fermentation. SSF is typically carried out at temperatures of 35-38° C., which is a compromise between the 50° C. optimum for cellulase and the 28° C. optimum for yeast. Consequently, this intermediate temperature can lead to substandard performance by both the cellulase enzymes and the yeast.

Fermentation

Fermentation of glucose resulting from the hydrolysis may produce one or more of the fermentation products selected from an alcohol, a sugar alcohol, an organic acid and a combination thereof.

The fermentation is typically conducted at a pH between about 4.0 and about 6.0, or between about 4.5 and about 6.0. To attain the foregoing pH range for fermentation, it may be necessary to add alkali to the stream comprising glucose.

In one embodiment of the invention, the fermentation product is an alcohol, such as ethanol or butanol. For ethanol production, the fermentation is typically carried out with a *Saccharomyces* spp. yeast. Glucose and any other hexoses present in the sugar stream may be fermented to ethanol by wild-type *Saccharomyces cerevisiae*, although genetically modified yeasts may be employed as well, as discussed below. The ethanol may then be distilled to obtain a concentrated ethanol solution. Butanol may be produced from glucose by a microorganism such as *Clostridium acetobutylicum* and then concentrated by distillation.

Xylose and arabinose that are derived from the hemicelluloses may also be fermented to ethanol by a yeast strain that naturally contains, or has been engineered to contain, the ability to ferment these sugars to ethanol. Examples of microbes that have been genetically modified to ferment xylose include recombinant *Saccharomyces* strains into which has been inserted either (a) the xylose reductase (XR) and xylitol dehydrogenase (XDH) genes from *Pichia stipitis* (U.S. Pat. Nos. 5,789,210, 5,866,382, 6,582,944 and 7,527, 927 and European Patent No. 450530); or (b) fungal or bacterial xylose isomerase (XI) gene (U.S. Pat. Nos. 6,475,768 and 7,622,284). Examples of yeasts that have been genetically modified to ferment L-arabinose include, but are not limited to, recombinant *Saccharomyces* strains into which genes from either fungal (U.S. Pat. No. 7,527,951) or bacterial (WO 2008/041840) arabinose metabolic pathways have been inserted.

Organic acids that may be produced during the fermentation include lactic acid, citric acid, ascorbic acid, malic acid, succinic acid, pyruvic acid, hydroxypropanoic acid, itaconoic acid and acetic acid. In a non-limiting example, lactic acid is the fermentation product of interest. The most well-known industrial microorganisms for lactic acid production from glucose are species of the genera *Lactobacillus, Bacillus* and *Rhizopus*.

Moreover, xylose and other pentose sugars may be fermented to xylitol by yeast strains selected from the group consisting of *Candida, Pichia, Pachysolen, Hansenula, Debaryomyces, Kluyveromyces* and *Saccharomyces*. Bacteria are also known to produce xylitol, including *Corynebacterium* sp., *Enterobacter liquefaciens* and *Mycobacterium smegmatis*.

In practice, the fermentation is typically performed at or near the temperature and pH optimum of the fermentation microorganism. A typical temperature range for the fermentation of glucose to ethanol using *Saccharomyces cerevisiae* is between about 25° C. and about 35° C., although the temperature may be higher if the yeast is naturally or genetically modified to be thermostable. The dose of the fermentation microorganism will depend on other factors, such as the activity of the fermentation microorganism, the desired fermentation time, the volume of the reactor and other parameters. It should be appreciated that these parameters may be adjusted as desired by one of skill in the art to achieve optimal fermentation conditions.

The fermentation may also be supplemented with additional nutrients required for the growth of the fermentation microorganism. For example, yeast extract, specific amino acids, phosphate, nitrogen sources, salts, trace elements and vitamins may be added to the hydrolyzate slurry to support their growth.

The fermentation may be conducted in batch, continuous or fed-batch modes with or without agitation. Preferably, the fermentation reactors are agitated lightly with mechanical agitation. A typical, commercial-scale fermentation may be conducted using multiple reactors. The fermentation microorganisms may be recycled back to the fermentor or may be sent to distillation without recycle.

Distillation

If ethanol or butanol is the fermentation product, the recovery is carried out by distillation, typically with further concentration by molecular sieves or membrane extraction.

The fermentation broth that is sent to distillation is a dilute alcohol solution containing solids, including unconverted cellulose, and any components added during the fermentation to support growth of the microorganisms.

Microorganisms are potentially present during the distillation depending upon whether or not they are recycled during the fermentation. The broth is preferably degassed to remove carbon dioxide and then pumped through one or more distillation columns to separate the alcohol from the other components in the broth. The mode of operation of the distillation system depends on whether the alcohol has a lower or a higher boiling point than water. Most often, the alcohol has a lower boiling point than water, as is the case when ethanol is distilled.

In those embodiments where ethanol is concentrated, the column(s) in the distillation unit is preferably operated in a continuous mode, although it should be understood that batch processes are also encompassed by the present invention. Heat for the distillation process may be introduced at one or more points either by direct steam injection or indirectly via heat exchangers. The distillation unit may contain one or more separate beer and rectifying columns, in which case dilute beer is sent to the beer column where it is partially concentrated. From the beer column, the vapour goes to a rectification column for further purification. Alternatively, a distillation column is employed that comprises an integral enriching or rectification section.

After distillation, the water remaining may be removed from the vapour by a molecular sieve resin, by membrane extraction, or other methods known to those of skill in the art for concentration of ethanol beyond the 95% that is typically achieved by distillation. The vapour may then be condensed and denatured.

An aqueous stream(s) remaining after ethanol distillation and containing solids, referred to herein as "still bottoms", is withdrawn from the bottom of one or more of the column(s) of the distillation unit. This stream will contain inorganic salts, unfermented sugars and organic salts.

When the alcohol has a higher boiling point than water, such as butanol, the distillation is run to remove the water and other volatile compounds from the alcohol. The water vapor exits the top of the distillation column and is known as the "overhead stream".

EXAMPLES

Determination of the Undissolved Solids Concentration in a Lignocellulosic Feedstock Slurry The determination of the undissolved solids (UDS) content in a slurry is carried out as follows.

A sample of slurry is dispensed into a plastic weigh dish and the slurry weight is recorded accurately using an analytical scale. A filter paper circle, appropriately sized for a Buchner funnel, is placed in an aluminum weighing tin and the combined weight of the tin and filter paper is recorded. After transferring the pre-weighed filter paper to the Buchner funnel, the pre-weighed slurry is passed through the filter paper to isolate the solids. Small volumes of de-ionized water are used to ensure that the solids are quantitatively transferred from the weigh dish to the Buchner funnel. The solids are then washed using excess deionized water, after which the washed sample and filter paper are transferred into the pre-weighed aluminum tin. Care should be taken to ensure the solids are quantitatively transferred. After drying the aluminum tin in a 105° C. oven overnight, the contents are weighed accurately and the UDS is quantified by determining, as a percent, the number of grams of dry solids per gram of slurry.

Configuration of the High Shear in-Line Mixer System

A high shear in-line mixing system was designed to test the ability of the high shear in-line mixers to combine alkali and enzyme with high consistency pretreated feedstock slurry. In Examples 1-3, a potassium iodide tracer was substituted for alkali or enzyme, but is expected to behave similarly.

The system comprised the following major pieces of equipment: (i) a Liberty Process progressive cavity pump, model 21-18 (slurry pump), commercially available from Liberty Process Equipment, installed with a variable-frequency drive (VFD); (ii) a Sulzer® SX-HP-8-8 high shear in-line mixer installed with a 20 hp motor and VFD; and (iii) a Watson Marlow Bredel SPX 15 hose pump.

The process equipment in the high shear in-line dispersion system was configured as follows. The system included a hopper mounted over the progressive cavity pump. The progressive cavity pump fed a 4 inch line towards the high shear in-line mixer. Between the pump and the in-line mixer, a hose pump was used to inject potassium iodide tracer or cellulase enzyme into the 4 inch pipe via ⅜ inch tubing. A small tank fed the hose pump. The high shear in-line mixer had 3 inch diameter process connections. Downstream of the mixer, the 3 inch connection was reduced to a 2 inch fitting via a reducer, with subsequent effluent collection in open top barrels.

Operation of the High Shear in-Line Mixer System

Wheat straw was pretreated with sulfuric acid as set forth in U.S. Pat. No. 7,754,457 (incorporated herein by reference). The acid pretreated feedstock had a consistency of approximately 24 wt % undissolved solids. The consistency of the acid pretreated feedstock slurry was adjusted to approximately 21 wt % undissolved solids (UDS). This was accomplished by adding water via the injection system upstream of the high shear in-line mixer, running the in-line mixer and re-circulating the feedstock slurry back to the hopper. The flow rate out of the hose pump located upstream of the high shear in-line mixer was measured at 800 mL/min. With the pumps configured, tracer or enzyme was added to the small tank that fed the hose pump. To ensure the presence of tracer at the exit of the system when the sample was taken, the hose pump was started first, the high shear in-line mixer second and finally the progressive cavity pump. There was at least a 30 second delay before taking a sample to purge the pipe between the injection port and the sample location. Two cross-sectional samples were sliced from a long sample taken from the 2 inch port.

Example 1

Side-Wall Injection of Tracer Solution into the High Shear in-Line Mixer

In this example, the ability of the high shear in-line mixer to disperse potassium iodide tracer into acid pretreated lignocellulosic feedstock having 21% UDS was examined. The injection line was installed onto the side-wall of the 4 inch process pipe upstream of the mixer.

Two experiments were carried out as described below. Both experiments involved injecting potassium iodide tracer into the high consistency acid pretreated material, prepared as set forth above. The high shear in-line mixer was operated at different speeds for each experiment as specified below.

Side-Wall Injection Experiment 1

Downstream of the high shear in-line mixer, samples of the pretreated lignocellulosic feedstock were taken and dissected into thirds. Iodide concentration was determined in each dissected sample. The high shear in-line mixer was operated at two different speeds: 75% and 50% of the maximum speed. Two cross-sectional samples were taken at each speed.

The data from the analysis of the samples taken are shown in Table 1 below and plotted in FIG. 2. Each sample was diluted with water and then the iodide concentration was determined using an iodide selective probe.

TABLE 1

Iodide Concentration for Experiment 1

| | | Iodide Concentration (ppm) | |
|---|---|---|---|
| Mixing Speed | Sample Side | Sample # 1 | Sample #2 |
| 50% | L | 401.5 | 418.6 |
| | M | 403.2 | 413.4 |
| | R | 404.9 | 416.9 |
| | Mean | 403.2 | 416.3 |
| | Standard Deviation | 1.70 | 2.65 |
| 75% | L | 360.2 | 383.5 |
| | M | 357.2 | 380.3 |
| | R | 369.4 | 385.1 |
| | Mean | 362.3 | 383.0 |
| | Standard Deviation | 6.36 | 2.44 |

Figure 2:
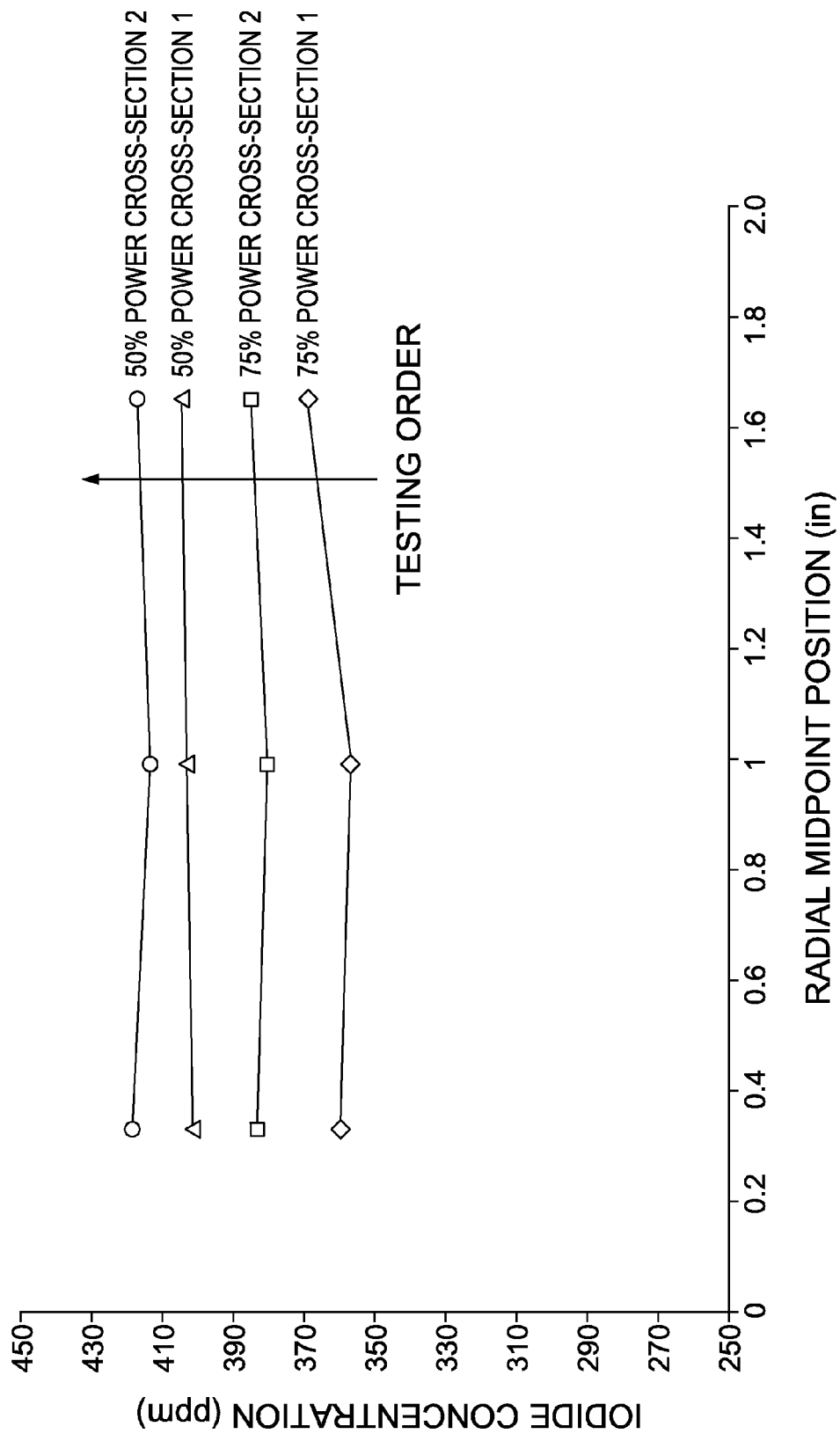
FIG. 2 is a graph showing the iodide concentration (ppm) verses the distance in inches along the horizontal plane from the injection site on the side wall of a pipe to the center of a slice of a slurry (referred to as the radial midpoint position in inches). An injection line for introducing the potassium iodide was installed onto the side wall of the pipe. The slices were obtained by the dissection of a cross-sectional sample as depicted in FIG. 1A. Two cross-sectional samples were taken at both 50% power (open circles and open triangles) and 75% power (open squares and open diamonds).

In FIG. 2, the radial midpoint distance shown is the distance along the horizontal plane from the injection site to the center of each slice of acid pretreated slurry when sectioned as shown in FIG. 1A.

It should be understood that the measured level of iodide shown in FIG. 2 cannot be compared among the specific tests, as the potassium iodide dosing pump was not kept at a constant set-point between runs. Overall, the data show that all power levels tested resulted in near ideal dispersion of the potassium iodide tracer.

Side-Wall Injection Experiment 2

The second experiment was similar to Experiment 1, but the cross-sectional samples were dissected into 8 sections (FIG. 1B), instead of 3. Each dissected section was subsequently analyzed individually for iodide concentration.

The high shear in-line mixer was run at 4 speeds (0, 10, 33 and 50% of maximum speed) and two cross-sections were taken at each speed.

Figure 1B:
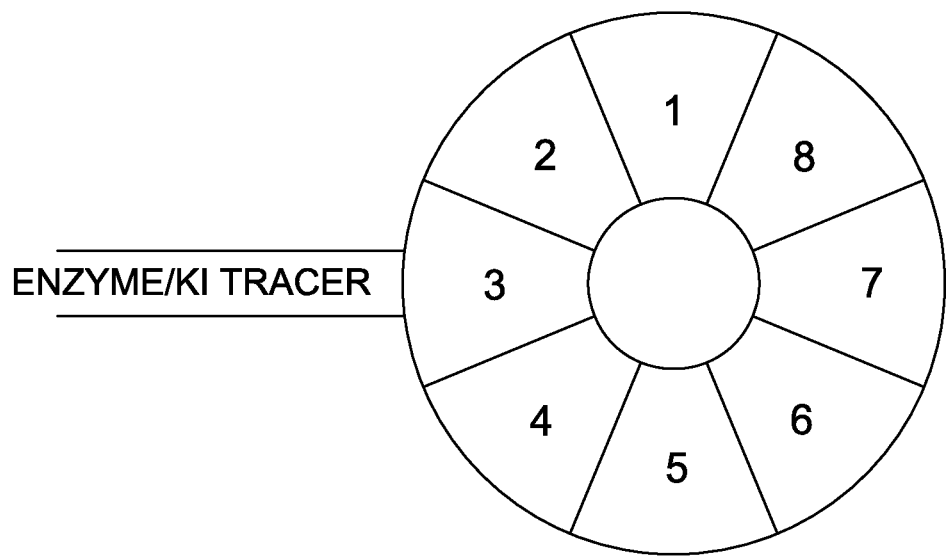

It should be pointed out that, for this experiment set, the relative location of numbered samples to the injection site do not correlate to FIG. 1B. That is, the orientation of the cross-section was not recorded in relation to the injection site.

Figure 3:
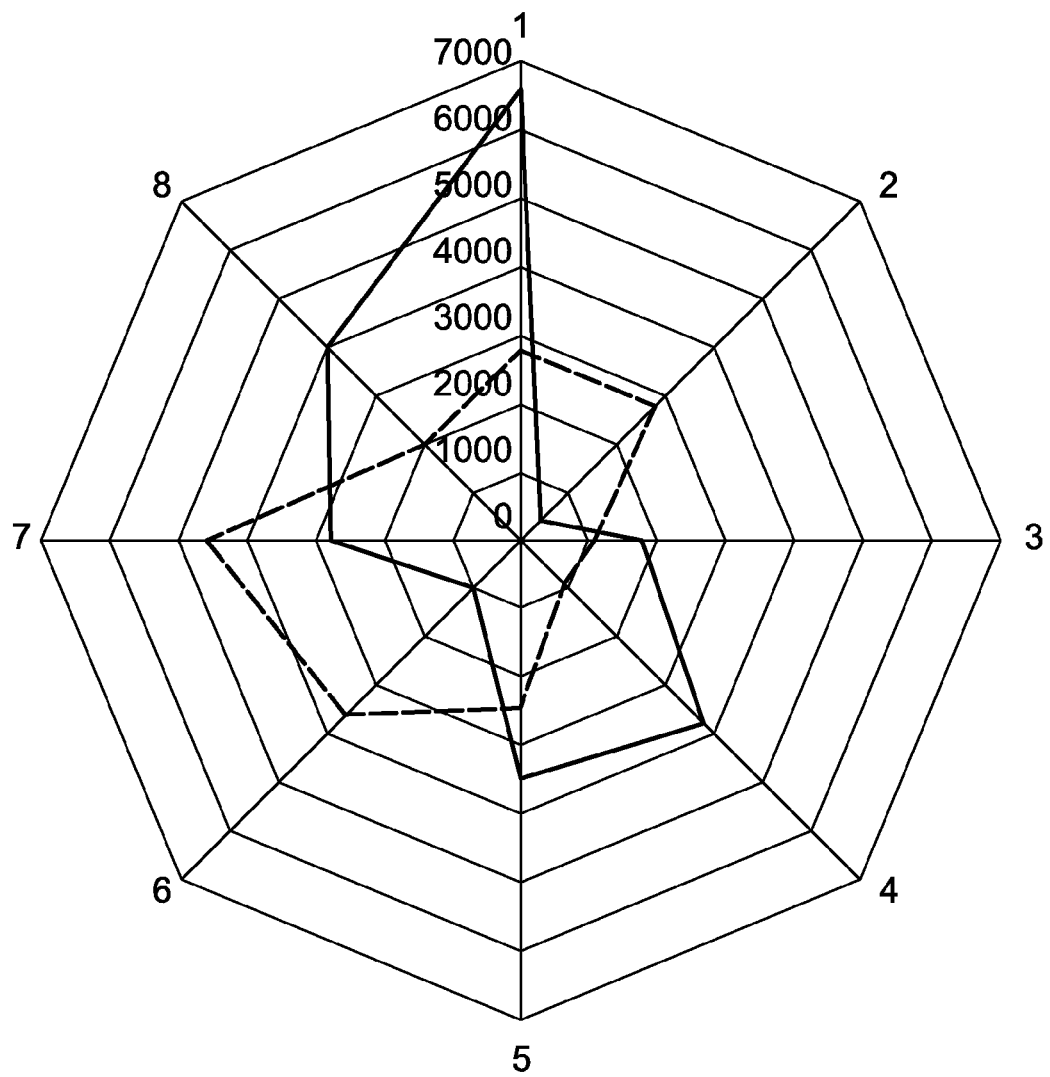
FIG. 3 shows the iodide concentration (ppm) of each of the 8 sections of a cross-sectional slice obtained as shown in FIG. 1B when the in-line high shear mixer was operated at 33% of its maximum mixing power. Two cross-sectional slices were taken at this mixing speed. An injection line for introducing the potassium iodide was installed onto the side wall of the pipe.
Figure 4:
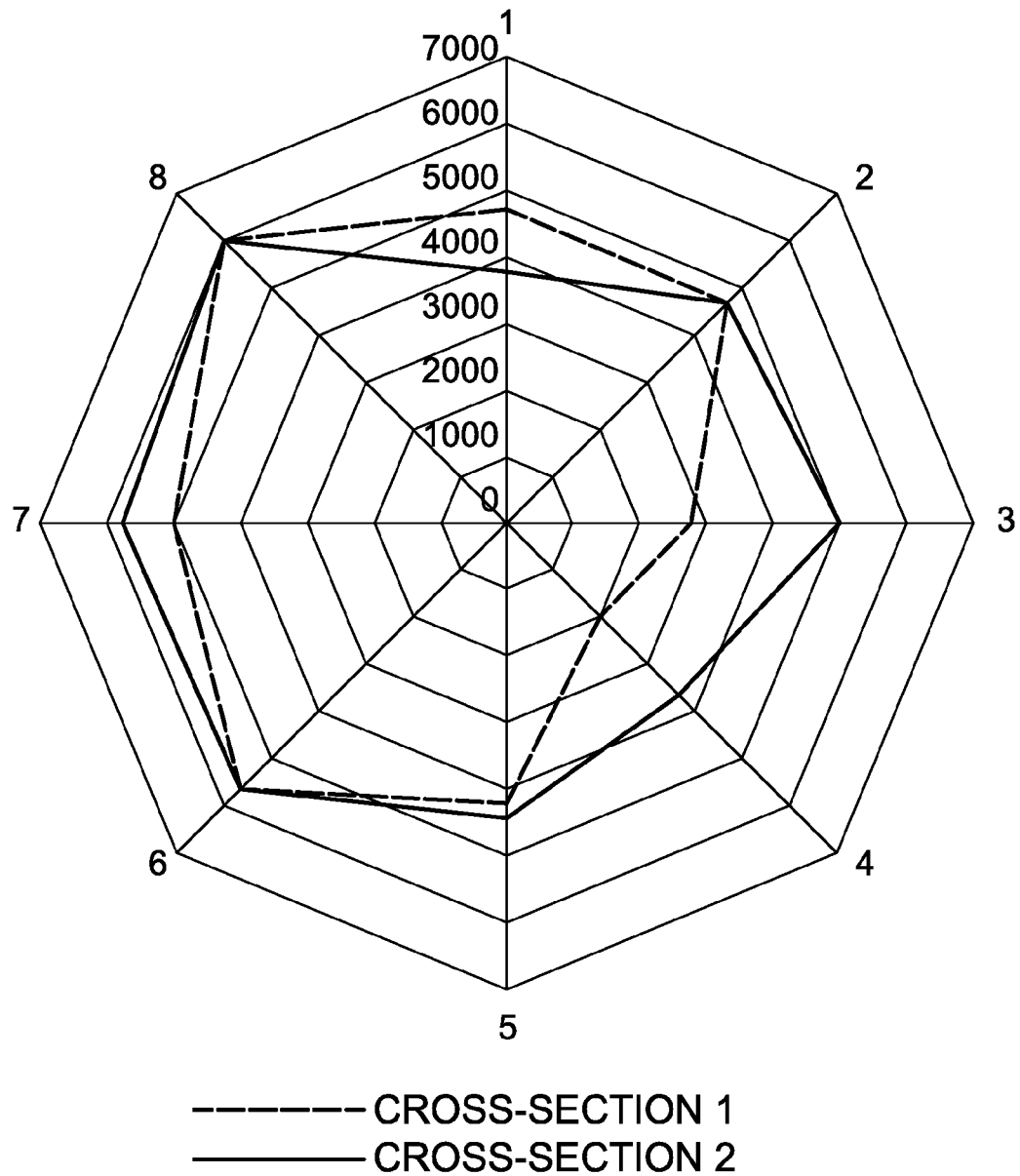
FIG. 4 shows the iodide concentration (ppm) of each of the 8 sections of a cross-sectional slice dissected as shown in FIG. 1B. The in-line high shear mixer was operated at 50% of its maximum mixing power. Two cross-sectional slices were taken at this mixing speed. An injection line for introducing the potassium iodide was installed onto the side wall of the pipe.

FIGS. 3 and 4 show the 8 potassium iodide tracer points around the center point for 33% and 50% high shear in-line mixer speeds.

When the mixer was set to 50% of the maximum speed, the potassium iodide tracer was evenly distributed throughout the cross-section of the pipe as seen in FIG. 4. The largest deviation from the average concentration in cross-section 2 was 25%.

Example 2

Injection of Tracer Along the Center-Line of the High Shear in-Line Mixer Using a Single Quill In this example, the potassium iodide tracer was injected at a central point inside the process pipe using a single quill with the outlet facing downstream of the direction of slurry flow. As in the previous examples, the acid pretreated lignocellulosic feedstock contained 21 wt % UDS. Iodide distribution was examined at 33% and 50% of the maximum in-line mixer speed.

The samples were dissected into 9 sections as in Experiment 2 of Example 3. (See FIG. 1B for a depiction of the sections taken). The central section was not assayed for potassium iodide content.

Figure 5:
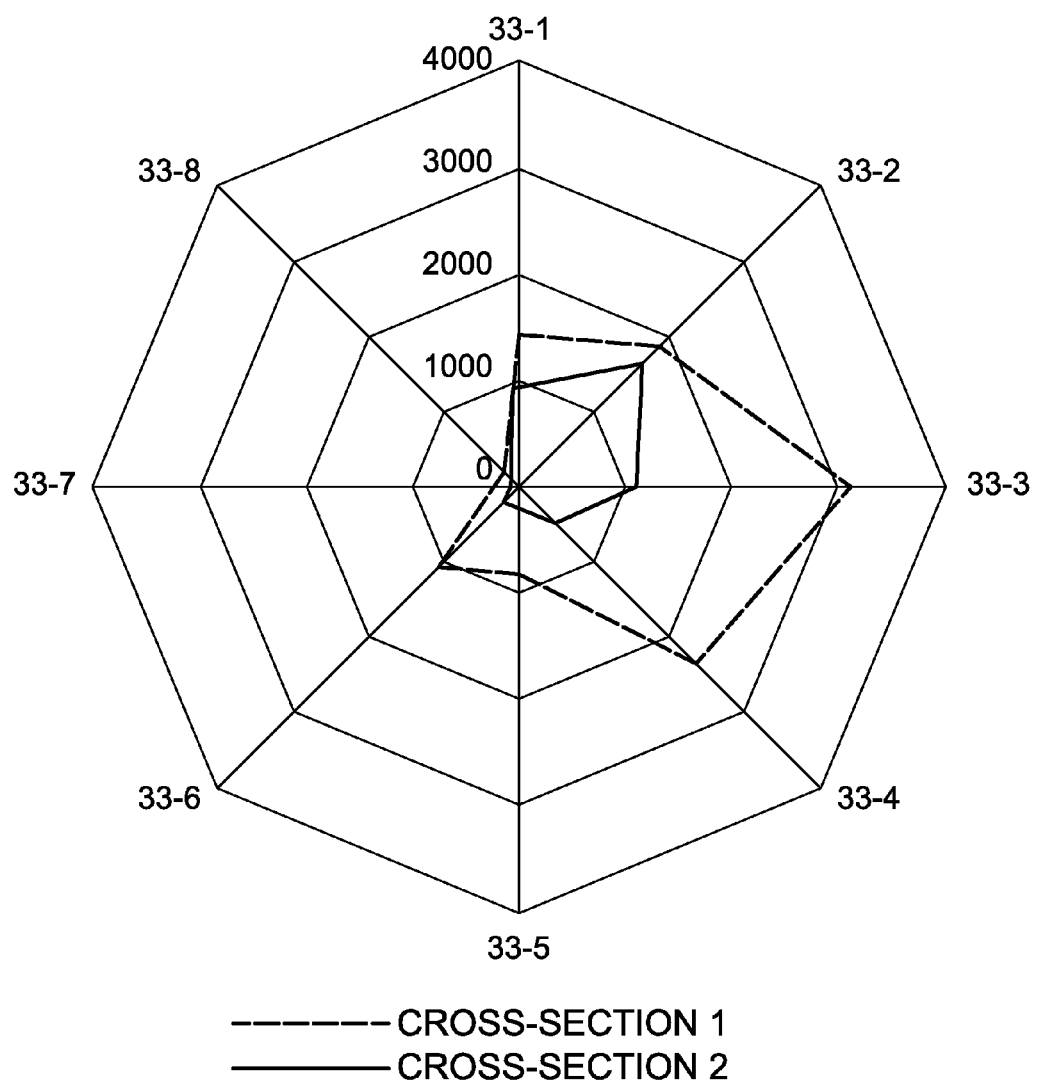
FIG. 5 shows the iodide concentration (ppm) of 8 sections of a cross-sectional slice dissected as shown in FIG. 1B when injection of the potassium iodide tracer was to the center of the pipe. The in-line high shear mixer was operated at 33% of its maximum mixing power.
Figure 6:
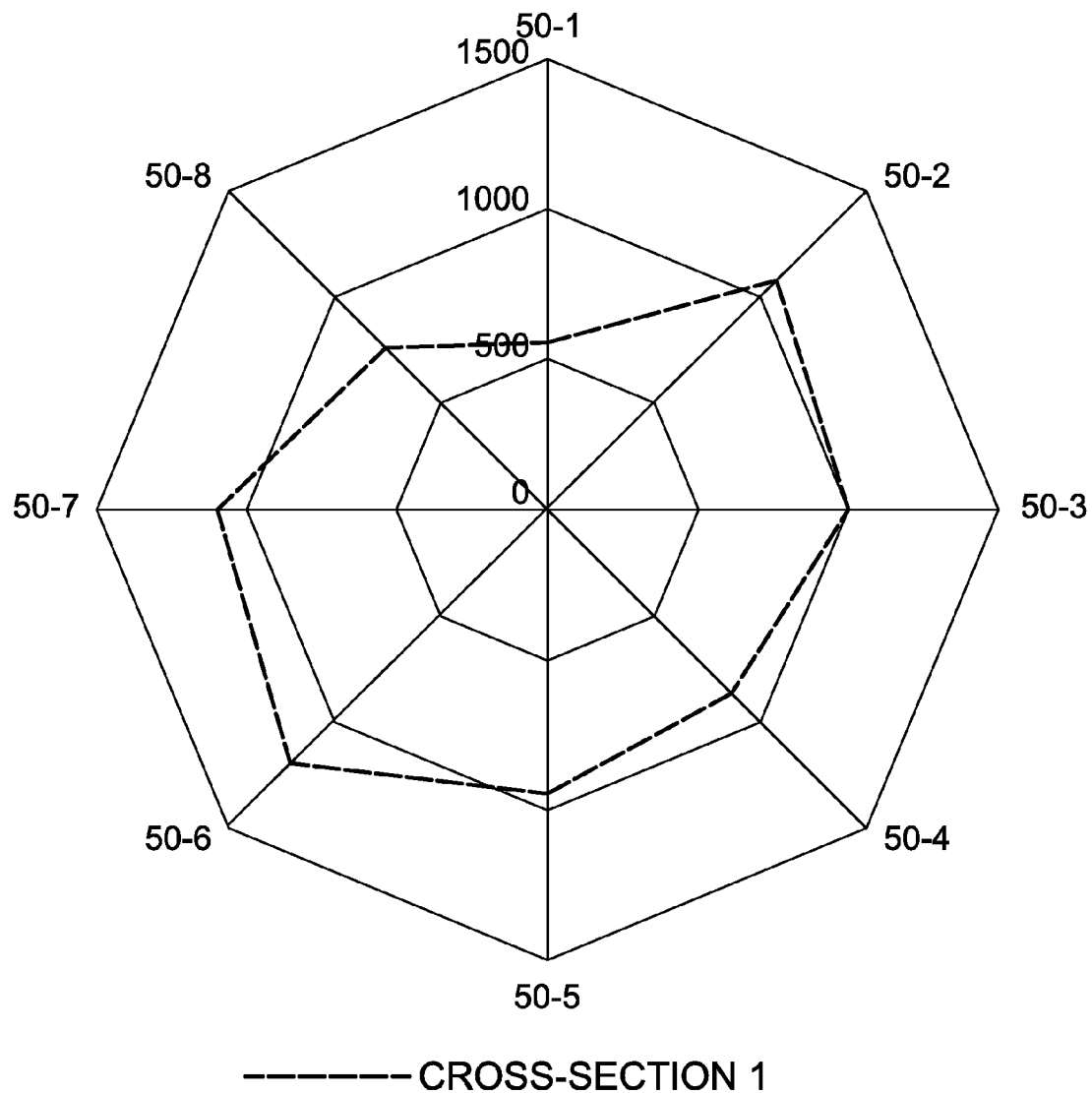
FIG. 6 shows the iodide concentration (ppm) of 8 sections of two cross-sectional slices dissected as shown in FIG. 1B when injection of the potassium iodide tracer was to the center of the pipe. The in-line high shear mixer was operated at 50% of its maximum mixing power.

FIGS. 5 and 6 show the iodide concentration around the center point, at 33% and 50% mixer speed, respectively, with samples 33-1 and 50-1 corresponding to the potassium iodide concentration at the top of the pipe.

At 50% of the maximum mixer speed, the potassium iodide tracer displays even distribution in the high consistency pretreated feedstock.

Example 3

Figure 7:
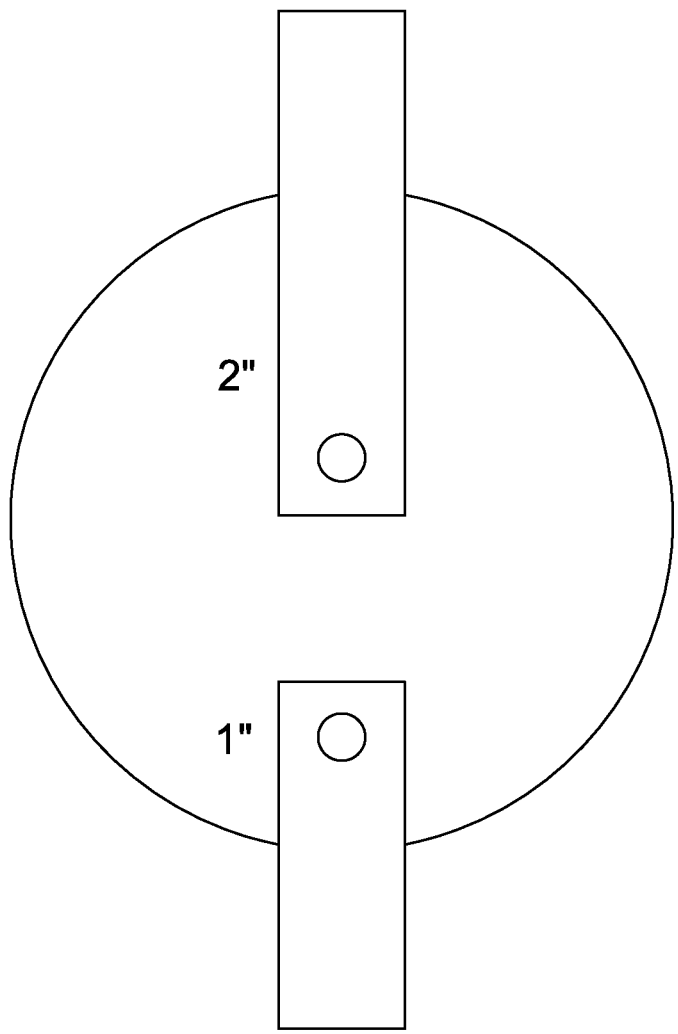
FIG. 7 depicts the set-up of an injection system for introducing potassium iodide tracer at two locations within a pipe. The acid pretreated lignocellulosic feedstock had an undissolved solids content of 21% (w/w). As shown in the figure, a 2 inch quill extends into the slurry from the top of the pipe with a hole ¼ inch from the end of the quill and a 1 inch quill extends into the slurry from the bottom of the pipe with a hole ¼ inch from the bottom of the pipe.

Injection of Tracer Along the Center-Line of the High Shear in-Line Mixer Using Two Quills In this example, the potassium iodide tracer was injected at two points inside the process pipe using two quills, each with their outlets facing downstream. The location of the injection site within the in-line mixer is depicted in FIG. 7. As in the previous examples, the acid pretreated lignocellulosic feedstock contained 21% UDS. Iodide distribution was examined at 33% and 50% maximum in-line mixer speed.

Figure 8:
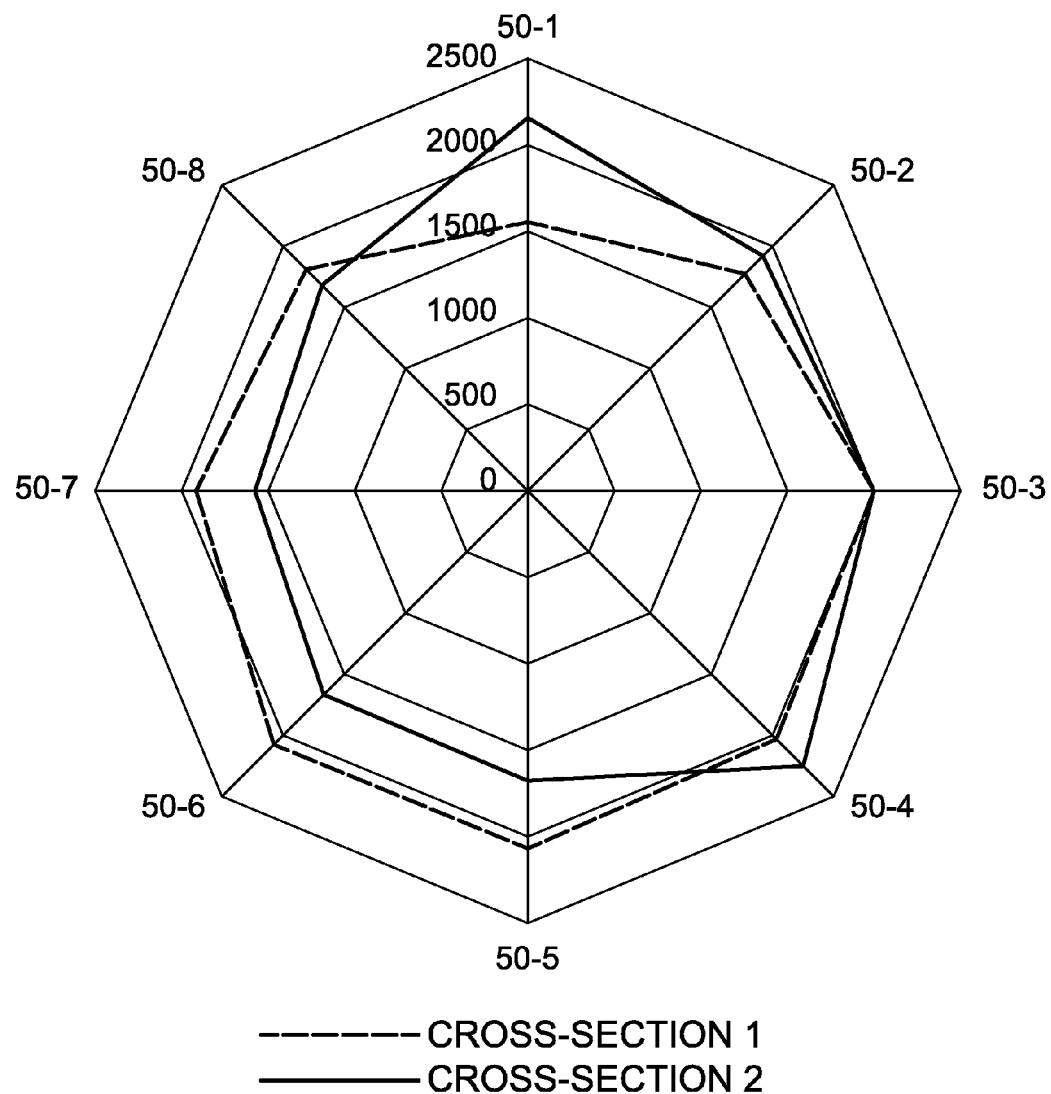
FIG. 8 shows the iodide concentration (ppm) of 8 sections of two cross-sectional slices dissected as shown in FIG. 4 when injection of the potassium iodide tracer was introduced at two locations in the pipe using injection quills as depicted in FIG. 7. The in-line high shear mixer was operated at 50% of its maximum mixing power.

The results are shown in FIG. 8. The two quill injection configuration exhibited the most even distribution at 50% mixing power (relative to maximum).

Example 4

Injection of Cellulase Enzyme Using a High Shear in-Line Mixer

The high consistency acid pretreated feedstock prepared as described above was injected with an enzyme mixture secreted by *Trichoderma reesei* comprising cellulase enzymes and beta-glucosidase using a high shear in-line mixer. The high shear in-line mixer system and the operating parameters that were utilized are those described previously.

The mean residence time of the slurry was calculated as follows. The internal volume of the mixer was 3.6 L and the flow rate was 40 L/min. Thus, V/Q=3.6 L/0.09 min=5.4 s.

Figure 9:
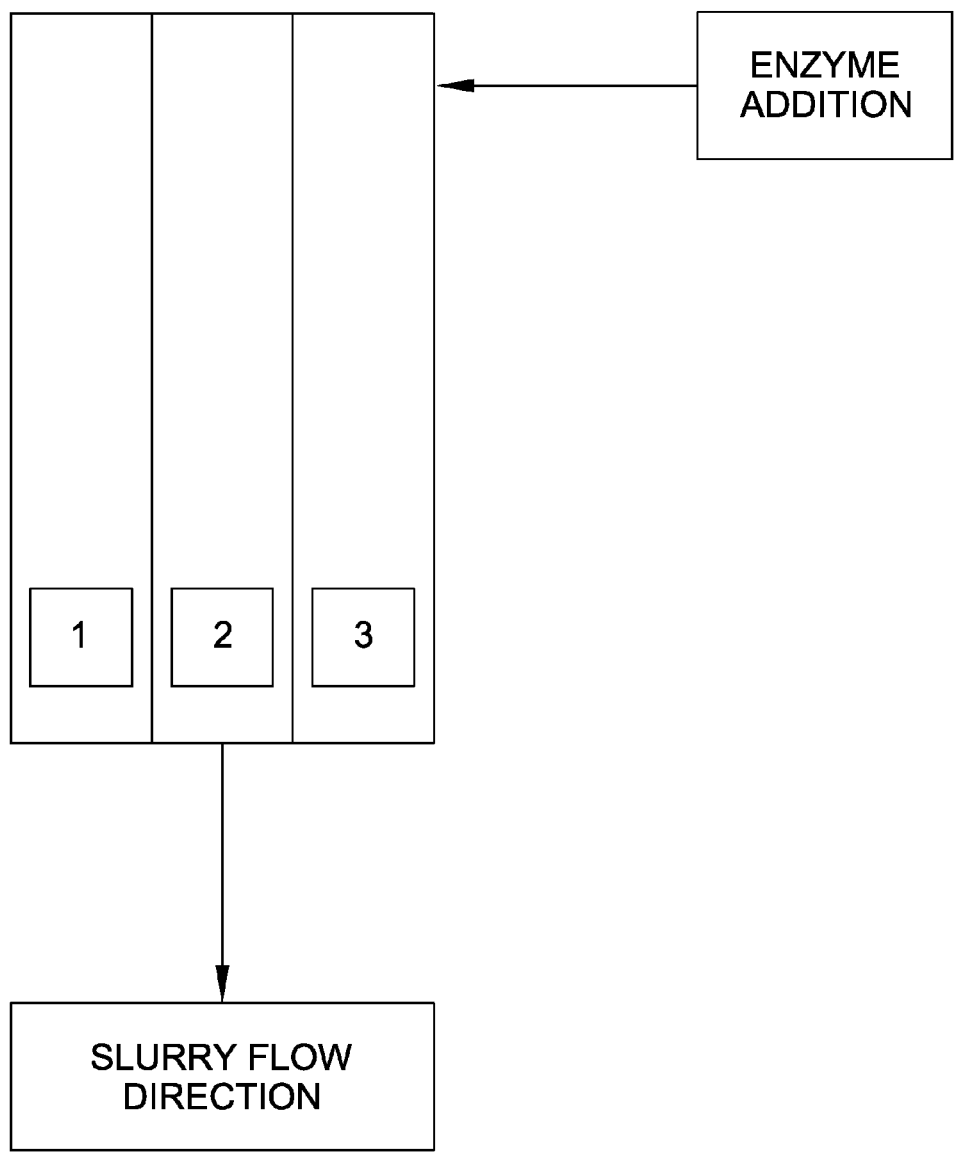
FIG. 9 depicts a cross-sectional slice of acid pretreated feedstock slurry sampled downstream of the in-line high shear mixer after addition of cellulase enzyme to the side wall of a pipe upstream of the mixer. The cross-sectional slice was dissected into three sections as depicted in the figure.

Downstream of the high shear in-line mixer, samples of the pretreated feedstock were taken, as described above. However, in this example, a thicker cross-sectional sample was taken, which was subsequently divided into three longitudinal sections, relative to the central axis of the pipe. The sections that were dissected are shown in FIG. 9.

The high shear in-line mixer speed was 50%, relative to maximum speed, for the enzyme injection.

The samples were run as unmixed hydrolysis in the lab for 6 hours, mixed thoroughly at 6 hours and then transferred to mixed hydrolysis for an additional 134 hours. The results were compared to a control (at 30 mg/g enzyme dosage). The control was an unmixed hydrolysis, followed by a mixed hydrolysis, where the enzyme was manually added and dispersed.

The experimental conditions for the unmixed and subsequent mixed hydrolysis are shown in Table 2 below.

TABLE 2

| Unmixed hydrolysis followed by mixed: experimental conditions | |
|---|---|
| Initial UDS, % | 21 |
| Batch size | 100 g |
| pH | 5.0 |
| Dosage, mg protein/g cellulose | 45 |
| Temperature ° C. | 50 |
| RPM of mixed hydrolysis | 250 |

Figure 10:
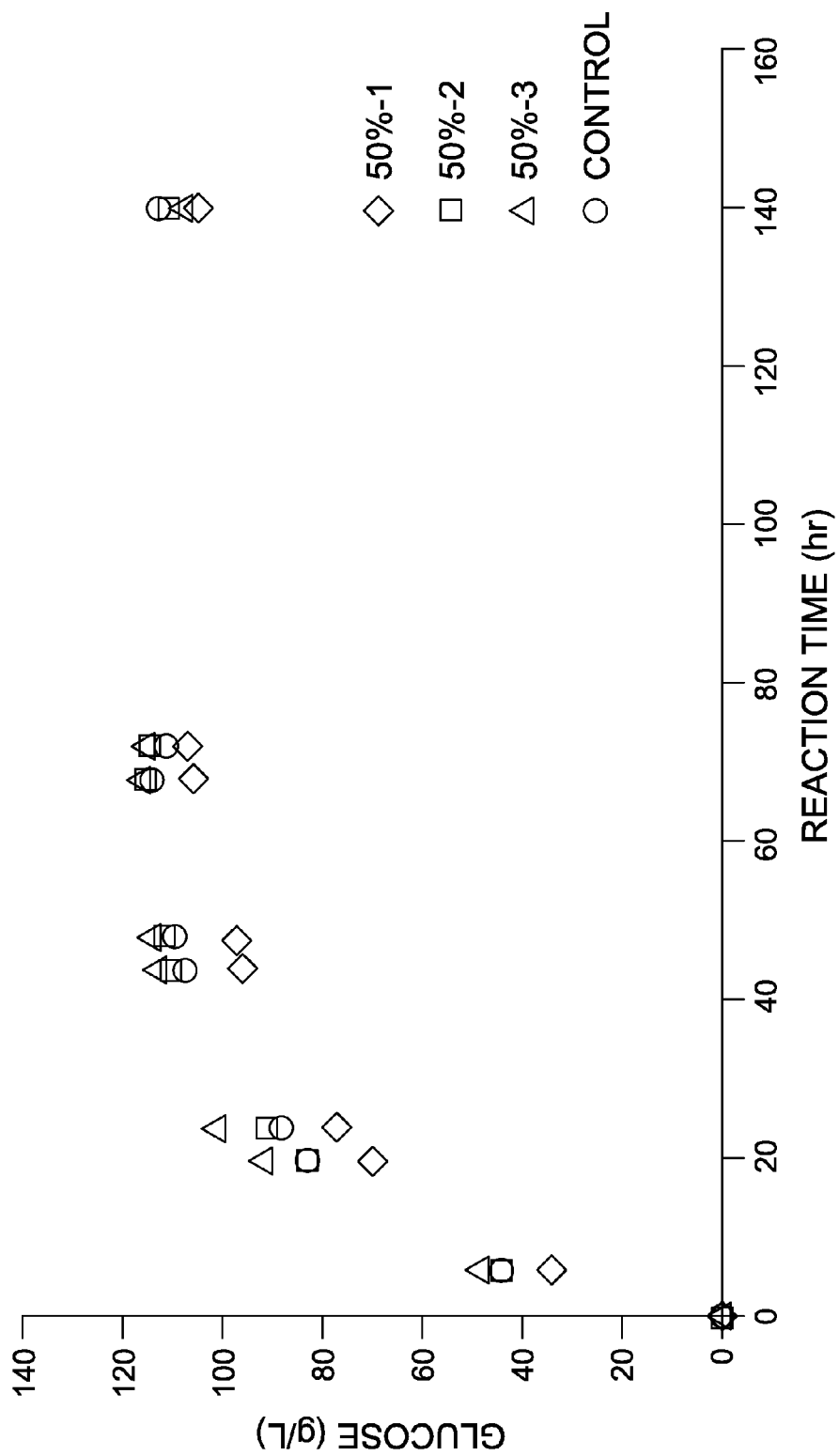
FIG. 10 is a graph showing glucose concentration verses reaction time for acid pretreated lignocellulosic feedstock slurry comprising cellulase enzyme injected as described in FIG. 9. The high shear in-line mixer was operated at 50% of its maximum speed. The dissected samples (depicted as diamonds, squares and triangles in the figure) were subjected to an unmixed hydrolysis for 6 hours, then thoroughly mixed, and subsequently transferred to mixed hydrolysis for an additional 134 hours. Also included in the figure are results for a control (circle) in which the enzyme was manually added and dispersed.

FIG. 10 shows the results of the hydrolyses for the three longitudinal sections sampled (labeled 50%-1 (diamonds), 50%-2 (squares) and 50%-3 (triangles)) verses the control (circles). The results are shown as glucose concentration (g/L) as a function of reaction time (hr).

The results in FIG. 10 show that the glucose concentration for each of the three samples hydrolyzed and the manually dispersed control were comparable throughout the time course. This data demonstrates that the exposure of cellulase enzyme to high shear during the high shear in-line mixing does not compromise the subsequent hydrolysis of the cellulose to glucose. Thus, high shear in-line mixing permits effective enzyme dispersion without loss of enzymatic hydrolysis productivity. One can also deduce from these results that cellulase enzyme activity was not reduced significantly by exposure to the high shear in-line mixer for the time period required to obtain good mixing.

Comparative Example 1

Acid pretreated slurry, prepared as described in Example 1-4, was subjected to a lab-scale rotor-stator dispersion device having two concentric, toothed rings within a chamber (IKA magicLAB Basic unit with Ultra Turrax® (UTL) module P/N R078310). The acid pretreated feedstock slurry was fed through the center of the device. A similar device is disclosed in U.S. Pat. No. 5,498,766 (supra). However, flow of the acid pretreated slurry through the device could not be achieved due to plugging of the pretreated feedstock slurry.

The invention claimed is:

1. A method for producing glucose from a lignocellulosic feedstock, said method comprising the steps of:
    (i) providing a pretreated lignocellulosic feedstock slurry in which at least a portion of the hemicellulose has been hydrolyzed during pretreatment;
    (ii) moving the pretreated slurry through a pipe, which pretreated slurry has an undissolved solids content of between about 15 and about 30 wt %;
    (iii) optionally adjusting the pH of the pretreated slurry to a pH that is compatible with cellulase enzyme;
    (iv) adding cellulase enzyme to said pretreated slurry to produce a slurry comprising cellulase enzyme, while maintaining the undissolved solids content of said pretreated slurry between about 15 and about 30 wt %;
    (v) dispersing the cellulase enzyme added in step (iv) in said pretreated slurry prior to any hydrolysis in a reactor by using a high shear in-line mixing device so as to impart shear to said pretreated slurry, thereby producing a pretreated slurry in which the cellulase enzyme is dispersed; and thereafter
    (vi) subjecting the pretreated slurry resulting from step (v) comprising dispersed cellulase enzyme to hydrolysis in the reactor so as to produce glucose from cellulose contained therein.

2. A method for producing glucose from a lignocellulosic feedstock, said method comprising the steps of:
    (i) providing a pretreated lignocellulosic feedstock slurry in which at least a portion of the hemicellulose has been hydrolyzed during pretreatment;
    (ii) moving the pretreated slurry through a pipe, which pretreated slurry has an undissolved solids content of between about 15 and about 30 wt %;
    (iii) optionally adjusting the pH of the pretreated slurry to a value that is compatible with cellulase enzyme;
    (iv) adding cellulase enzyme to said pretreated slurry to produce a slurry comprising cellulase enzyme, while maintaining the undissolved solids content of said pretreated slurry between about 15 and about 30 wt %;
    (v) dispersing the cellulase enzyme added in step (iv) in said pretreated slurry prior to any hydrolysis in a reactor by using a high shear in-line mixing device so as to impart shear to said pretreated slurry, thereby producing a pretreated slurry in which the cellulase enzyme is dispersed, which high shear in-line mixing device comprises one or more mixing element, wherein the ratio of the cross-sectional area of the one or more mixing element to the cross-sectional area of the pipe in the same lateral plane is between 0.01 and 2; and thereafter
    (vi) subjecting the pretreated slurry resulting from step (v) comprising dispersed cellulase enzyme to hydrolysis in the reactor so as to produce glucose from cellulose contained therein.

3. A method for producing glucose from a lignocellulosic feedstock, said method comprising the steps of:
    (i) providing a pretreated lignocellulosic feedstock slurry in which at least a portion of the hemicellulose has been hydrolyzed during pretreatment;
    (ii) moving the pretreated slurry through a pipe, which pretreated slurry has an undissolved solids content of between about 15 and about 30 wt %;
    (iii) optionally adjusting the pH of the pretreated slurry to a value that is compatible with cellulase enzyme;
    (iv) adding cellulase enzyme to said pretreated slurry to produce a slurry comprising cellulase enzyme, while maintaining the undissolved solids content of said pretreated slurry between about 15 and about 30 wt %;
    (v) dispersing the cellulase enzyme added in step (iv) in said pretreated slurry prior to any hydrolysis in a reactor by using a high shear in-line mixing device so as to impart shear to said pretreated slurry, thereby producing a pretreated slurry in which the cellulase enzyme is dispersed, wherein the residence time of the pretreated slurry in the high shear in-line mixing device is between 0.1 s and 60 s; and thereafter
    (vi) subjecting the pretreated slurry resulting from step (v) comprising dispersed cellulase enzyme to hydrolysis in the reactor so as to produce glucose from cellulose contained therein.

4. The method of claim 1, wherein the cellulase enzyme is added upstream of the high shear in-line mixing device, adjacent to the high shear in-line mixing device or a combination thereof.

5. The method of claim 1, wherein the reactor is an unmixed hydrolysis reactor, mixed hydrolysis reactor or a combination thereof.

6. The method of claim 1, wherein the cellulase enzyme comprises beta-glucosidase, Ce161, swollenin, expansin, lucinen, cellulose-induced protein or a combination thereof.

7. The method of claim 1, wherein the pretreated lignocellulosic feedstock slurry is an acid pretreated lignocellulosic feedstock slurry.

8. The method of claim 1, wherein the high shear in-line mixing device is a rotor-stator mixer having mixing elements mounted on a rotatable shaft that extends into the pipe.

9. The method of claim 1, wherein the shear rate imparted to the pretreated feedstock is between 10 and 10,000 $s^{-1}$.

10. The method of claim 9, wherein the shear rate imparted to the pretreated feedstock is between 100 and 1,000 $s^{-1}$.

11. The method of claim 1, wherein the feedstock slurry comprises feedstock having at least 20% cellulose and wherein greater than 90% by volume of the feedstock particles have a length between about ⅛ inch and about 6 inches.

12. A method for producing glucose from a lignocellulosic feedstock, said method comprising the steps of:
    (i) providing a pretreated lignocellulosic feedstock slurry;
    (ii) moving the pretreated feedstock slurry through a pipe, which pretreated slurry has an undissolved solids content of between about 15 and about 30 wt %;
    (iii) adding cellulase enzyme to said pretreated slurry to produce a slurry comprising cellulase enzyme;
    (iv) dispersing the cellulase enzyme added in step (iii) in said pretreated slurry prior to any hydrolysis in a reactor by using a high shear in-line mixing device, thereby producing a pretreated slurry comprising dispersed cellulase enzyme; and thereafter
    (v) subjecting the pretreated slurry comprising dispersed cellulase enzyme to hydrolysis in the reactor so as to produce glucose from cellulose contained therein.

* * * * *